United States Patent
Hermans et al.

(10) Patent No.: US 10,407,364 B2
(45) Date of Patent: Sep. 10, 2019

(54) HETEROGENEOUS CATALYSTS FOR THE OXIDATIVE DEHYDROGENATION OF ALKANES OR OXIDATIVE COUPLING OF METHANE

(71) Applicant: Wisconsin Alumni Research Foundation, Madison, WI (US)

(72) Inventors: Ive Hermans, Madison, WI (US); Joseph Thomas Grant, Madison, WI (US); Carlos Alberto Carrero Marquez, Madison, WI (US); Alessandro Chieregato, Madison, WI (US); Juan Mauricio Venegas, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 15/993,665

(22) Filed: May 31, 2018

(65) Prior Publication Data
US 2018/0290950 A1  Oct. 11, 2018

Related U.S. Application Data

(63) Continuation of application No. 15/260,649, filed on Sep. 9, 2016, now Pat. No. 10,011,540.
(Continued)

(51) Int. Cl.
*C07C 5/42* (2006.01)
*C07C 2/84* (2006.01)
(Continued)

(52) U.S. Cl.
CPC ............... *C07C 5/48* (2013.01); *B01J 21/02* (2013.01); *B01J 21/063* (2013.01); *B01J 23/20* (2013.01); *B01J 23/755* (2013.01); *B01J 27/22* (2013.01); *B01J 27/24* (2013.01); *B01J 35/1009* (2013.01); *B01J 35/1014* (2013.01); *B01J 35/1019* (2013.01); *B01J 35/1057* (2013.01);
(Continued)

(58) Field of Classification Search
None
See application file for complete search history.

(56) References Cited

U.S. PATENT DOCUMENTS 7,041,621 B2 * 5/2006 Ramani .................... B01J 23/56
423/651
2009/0326279 A1 * 12/2009 Tonkovich ............ B01F 5/0475
568/487
(Continued)

OTHER PUBLICATIONS

Mosuang et al., Relative stability of cubic and different hexagonal forms of boron nitride, Journal of Physics and Chemistry of Solids 63, 2002, pp. 363-368. (Year: 2002).*
(Continued)

*Primary Examiner* — Philip Y Louie
(74) *Attorney, Agent, or Firm* — Boyle Fredrickson S. C.

(57) ABSTRACT

Improved methods of oxidative dehydrogenation (ODH) of short chain alkanes or ethylbenzene to the corresponding olefins, and improved methods of oxidative coupling of methane (OCM) to ethylene and/or ethane, are disclosed. The disclosed methods use boron- or nitride-containing catalysts, and result in improved selectivity and/or byproduct profiles than methods using conventional ODH or OCM catalysts.

20 Claims, 23 Drawing Sheets

Related U.S. Application Data

(60) Provisional application No. 62/215,879, filed on Sep. 9, 2015.

(51) Int. Cl.

| | | |
|---|---|---|
| *B01J 27/24* | (2006.01) | |
| *C07C 5/48* | (2006.01) | |
| *B01J 21/02* | (2006.01) | |
| *B01J 21/06* | (2006.01) | |
| *B01J 23/20* | (2006.01) | |
| *B01J 23/755* | (2006.01) | |
| *B01J 27/22* | (2006.01) | |
| *B01J 35/10* | (2006.01) | |
| *B01J 35/00* | (2006.01) | |

(52) U.S. Cl.
CPC ............ *B01J 35/1061* (2013.01); *C07C 2/84* (2013.01); *B01J 35/0013* (2013.01); *C07C 2527/24* (2013.01); *Y02P 20/52* (2015.11)

(56) References Cited

U.S. PATENT DOCUMENTS

| 2010/0222623 A1* | 9/2010 | Ryan .................... C07C 5/48 585/654 |
| 2011/0144400 A1* | 6/2011 | Mian .................... B01J 23/14 585/440 |
| 2013/0072737 A1* | 3/2013 | Kustov ................. C07C 5/48 585/658 |

OTHER PUBLICATIONS

Sainsbury et al., Oxygen Radical Functionalization of Boron Nitride Nanosheets, Journal of the American Chemical Society, 2012, pp. 18758-18771. (Year: 2012).*

* cited by examiner

HETEROGENEOUS CATALYSTS FOR THE OXIDATIVE DEHYDROGENATION OF ALKANES OR OXIDATIVE COUPLING OF METHANE

CROSS REFERENCE TO RELATED APPLICATIONS

This application is a continuation of U.S. application Ser. No. 15/260,649 filed on Sep. 9, 2016, which claims the benefit of U.S. provisional Application No. 62/215,879 filed on Sep. 9, 2015. Each of these applications is incorporated by reference herein in its entirety.

STATEMENT REGARDING FEDERALLY SPONSORED RESEARCH OR DEVELOPMENT

N/A

FIELD OF THE INVENTION

The disclosure relates to methods of catalyzing reactions that occur under oxidative conditions, such as the oxidative dehydrogenation of alkanes or the oxidative coupling of methane, using a catalyst containing boron and/or nitride.

BACKGROUND OF THE INVENTION $C_3$ and $C_4$ olefins, such as propylene (propene), 1-butene, isobutene and butadiene, are widely used starting materials in the industrial synthesis of a variety of important chemical products. The principal industrial method for producing $C_3$ and $C_4$ olefins is steam cracking, a petrochemical process in which saturated hydrocarbons are broken down into smaller, often unsaturated, hydrocarbons. The products obtained by steam cracking depend on the composition of the feed, the hydrocarbon-to-steam ratio, and on the cracking temperature and furnace residence time. For example, a feed composition that primarily contains ethane (ethane cracking) would result in high ethylene yields, while a feed composition including larger hydrocarbons, such as naptha (naptha cracking), would result in a larger yield of $C_3$ and $C_4$ olefins.

Over the last decade, the demand for $C_3$ and $C_4$ olefins has outstripped supply from traditional cracker units, and this trend is expected to accelerate over the next decade. For example, the current world demand for propene is around 100 million metric tons per year (MTA), and is expected to increase significantly over the next five years. This trend is primarily due to the availability of cheap shale gas, prompting many chemical companies to convert their naphtha crackers into ethane crackers, thus shifting production towards ethylene and away from longer chain $C_3$ and $C_4$ olefins. Accordingly, the demand for $C_3$ and $C_4$ olefins is growing faster than can be supplied by only cracking.

Because $C_3$ and $C_4$ olefin production by conventional steam cracking has not kept pace with rising demand, several alternative "on-purpose" olefin production technologies that convert short chain alkanes to the corresponding olefins have been developed. Examples include the catalytic dehydrogenation (DH) of short chain alkanes, such as propane, to the corresponding olefin, such as propene, using a supported $CrO_x/Al_2O_3$ catalyst ("CATOFIN®" (Lummus)), a Pt/Sn alloy supported on $Al_2O_3$ ("OLEFLEX™" (UOP)), or Pt/Sn supported on Zn-aluminate with co-fed steam ("STAR®" (Uhde)) (see Sattler et al., Chem. Rev., 2014, 114 (20), 10613-10653).

These and other currently used on-purpose dehydrogenation technologies are energy intensive, because the dehydrogenation reaction is highly endothermic. Furthermore, because they require high temperature conditions, they result in substantial catalyst deactivation due to the formation of coke. Thus, they require continuous catalyst regeneration. In addition, these processes may require substantially reduced pressure to shift the dehydrogenation equilibrium towards the desired products, further contributing to the high production costs associated with these methods.

Oxidative dehydrogenation (ODH), the catalytic dehydrogenation of feedstock alkanes in the presence of oxygen, is an intriguing alternative to conventional dehydrogenation that addresses each of the disadvantages of current DH technology. When oxygen is co-fed to act as a reactant, the reaction thermodynamics are altered such that the resulting net reaction is exothermic. Accordingly, the reaction can proceed at much lower reaction temperatures, resulting in decreased energy costs and increased catalyst stability. Oxygen in the feed stream also eliminates coke formation on the catalyst surface and thus creates no need for catalyst regeneration.

Despite these purported advantages, industrial-scale ODH processes have not been implemented, due to poor control of unwanted side-reactions (mainly the over-oxidation of olefin to CO and $CO_2$), which results in low olefin selectivity at conversions necessary for industrial implementation. For example, existing catalysts for propane ODH typically provide ~50-60% selectivity to propene at 10% propane conversion, with the byproducts largely made up of CO and $CO_2$. As a result, even after more than 30 years of research into catalysis development for ODH (almost entirely focused on supporting vanadium oxide on amorphous oxide supports (e.g., $SiO_2$, $Al_2O_3$, $TiO_2$, $CeO_2$, $ZrO_2$) and structured oxides (e.g., MCM-41, SBA-15)), ODH has not been successfully used in the industrial-scale production of $C_3$ and $C_4$ olefins.

Accordingly, there is a need in the art for improved methods and catalysts for the oxidative dehydrogenation of $C_3$-$C_5$ alkanes to the corresponding olefins.

BRIEF SUMMARY

We disclose herein new and improved methods for catalyzing the oxidative dehydrogenation of $C_2$-$C_5$ alkanes or ethylbenzene to the corresponding $C_2$-$C_5$ olefins or styrene, as well as improved methods for catalyzing the oxidative coupling of methane to form ethane and/or ethylene. The improved methods use catalysts containing boron, nitride, or both, to substantially increase selectivity (and productivity) for the desired olefin reaction product, while greatly decreasing the production of unwanted byproducts, such as CO and $CO_2$. In a non-limiting example, use of the disclosed catalyst for ODH of propane to propene (ODHP) provided 77% propene selectivity at 17% propane conversion, with the byproducts being primarily ethylene, and with negligible $CO_x$ formation. The exemplary catalyst stayed active over 8 days with no need for regeneration treatment, showing a marked improvement in reactivity over this time period.

Accordingly, the disclosure encompasses a method of making one or more desired chemical products. The method includes the step of contacting a heterogeneous catalyst comprising boron, nitride, or both, with oxygen and one or more liquid or gaseous reactants. The one or more desired chemical products are formed by a process catalyzed by the heterogeneous catalyst. The processes that can be catalyzed by the heterogeneous catalyst include oxidative dehydrogenation (ODH) or oxidative methane coupling (also known as oxidative coupling of methane, OCM).

In some embodiments, the process catalyzed by the heterogeneous catalyst is not zero order with respect to oxygen.

In some embodiments, the liquid or gaseous reactant is an alkane, the process catalyzed by the heterogeneous catalyst is oxidative dehydrogenation, and the one or more desired chemical products are olefins. In some such embodiments, the alkane is a $C_3$-$C_5$ alkane, including without limitation a $C_3$-$C_5$ n-alkane or iso-alkane. In some such embodiments, the alkane is a $C_4$-$C_5$ alkane, including without limitation a $C_3$-$C_4$ n-alkane or iso-alkane. In some such embodiments, the $C_3$-$C_4$ alkane is propane, n-butane, or isobutane, and the one or more desired chemical products may include propene, isobutene, 1-butene, 2-butene, and/or butadiene.

In some embodiments, the liquid or gaseous reactant is a hydrocarbon comprising an alkyl group, the process catalyzed by the heterogeneous catalyst is oxidative dehydrogenation, and the one or more desired chemical products include one or more hydrocarbons comprising an alkenyl group. In some such embodiments, the hydrocarbon comprising an alkyl group is ethylbenzene, and the one or more desired chemical products include styrene.

In some embodiments, the method maintains a greater than 70% selectivity for the desired chemical products (e.g., olefins) at 10% to 20% conversion of the alkane. In some such embodiments, the method maintains a greater than 77% selectivity for the olefin at 10% to 20% conversion of the alkane. In some such embodiments, the method maintains a greater than 80% selectivity for the olefin at 10% to 20% conversion of the alkane.

In some embodiments, the alkane is propane and the desired chemical products include propene. In some embodiments, the alkane is n-butane and the desired chemical products include 1-butene and/or 2-butene. In some embodiments, the alkane is isobutane and the desired chemical products include isobutene.

In some embodiments, the one or more desired chemical products further include ethylene. In some such embodiments, the method exhibits a higher selectivity towards ethylene than it does towards undesired CO or $CO_2$ byproducts. In some such embodiments, the method exhibits a 90% or greater selectivity for the propene, ethylene and other desired products (e.g., other olefins) together.

In some embodiments, the one or more liquid or gaseous reactants include methane, the heterogeneous catalyst catalyzes oxidative coupling of methane, and the one or more desired chemical products include ethane and/or ethylene. In some embodiments, the heterogeneous catalyst is contacted with natural gas.

In some embodiments, the heterogeneous catalyst includes a boron- or nitride-containing compound.

In some embodiments, the heterogeneous catalyst includes a nitride-containing compound. In some such embodiments, the nitride-containing compound is B-nitride, Si-nitride, Ti-nitride, or Al-nitride.

In some embodiments, the heterogeneous catalyst includes a boron-containing compound. In some such embodiments, the boron-containing compound B-nitride, B-carbide, Ti-boride, Ni-boride, or Nb-boride.

In some embodiments, the boron- or nitride-containing compound is boron nitride. In some such embodiments, the boron nitride has a surface area of greater than 5 $m^2$ $g^{-1}$, greater than 10 $m^2$ $g^{-1}$, greater than 20 $m^2$ $g^{-1}$, greater than 30 $m^2$ $g^{-1}$, greater than 40 $m^2$ $g^{-1}$, greater than 50 $m^2$ $g^{-1}$, greater than 60 $m^2$ $g^{-1}$, greater than 70 $m^2$ $g^{-1}$, greater than 80 $m^2$ $g^{-1}$, greater than 90 $m^2$ $g^{-1}$, greater than 100 $m^2$ $g^{-1}$, greater than 110 $m^2$ $g^{-1}$, greater than 120 $m^2$ $g^{-1}$, greater than 130 $m^2$ $g^{-1}$, greater than 140 $m^2$ $g^{-1}$, greater than 150 $m^2$ $g^{-1}$, greater than 180 $m^2$ $g^{-1}$, greater than 200 $m^2$ $g^{-1}$, greater than 250 $m^2$ $g^{-1}$, greater than 300 $m^2$ $g^{-1}$, greater than 350 $m^2$ $g^{-1}$, greater than 400 $m^2$ $g^{-1}$, greater than 450 $m^2$ $g^{-1}$, or greater than 500 $m^2$ $g^{-1}$. In some such embodiments, the boron nitride has a surface area range of about 5 $m^2$ $g^{-1}$ to 550 $m^2$ $g^{-1}$, about 9 $m^2$ $g^{-1}$ to 550 $m^2$ $g^{-1}$, about 50 $m^2$ $g^{-1}$ to 550 $m^2$ $g^{-1}$, about 100 $m^2$ $g^{-1}$ to 500 $m^2$ $g^{-1}$, or about 100 $m^2$ $g^{-1}$ to 200 $m^2$ $g^{-1}$. In certain exemplary embodiments, the boron nitride has a surface area of about 150 $m^2$ $g^{-1}$, about 180 $m^2$ $g^{-1}$, about 200 $m^2$ $g^{-1}$, about 250 $m^2$ $g^{-1}$, about 300 $m^2$ $g^{-1}$, about 350 $m^2$ $g^{-1}$, about 450 $m^2$ $g^{-1}$, or about 500 $m^2$ $g^{-1}$.

In some embodiments, the boron nitride is in the form of hexagonal boron nitride (h-BN), boron nitride nanotubes (BNNTs), boron nitride nanosheets (BNNSs), boron nitride nanoribbons (BNNRs) or boron nitride nanomeshes (h-BN nanomeshes).

In some embodiments, the boron nitride further includes oxygen atoms. In some such embodiments, the oxygen atoms are covalently bonded to boron, nitrogen, and/or other oxygen atoms. In some embodiments, the oxygen atoms may be bonded (functionalized) to the surface of the boron nitride.

In some embodiments, the heterogeneous catalyst comprises an oxynitride.

In some embodiments, the heterogenous catalyst is not simultaneously contacted with nitrogen.

In some embodiments, the oxygen and one or more liquid or gaseous reactants are in a reactant stream that is contacted with the heterogeneous catalyst. In some such embodiments, the reactant stream includes from 0% to 70% nitrogen by volume.

Further objects, features and advantages of the invention will be apparent from the following detailed description when taken in conjunction with the accompanying drawings.

BRIEF DESCRIPTION OF THE DRAWINGS

The disclosure will be better understood and features, aspects and advantages other than those set forth above will become apparent when consideration is given to the following detailed description thereof. Such detailed description makes reference to the following drawings.

Figure 1:
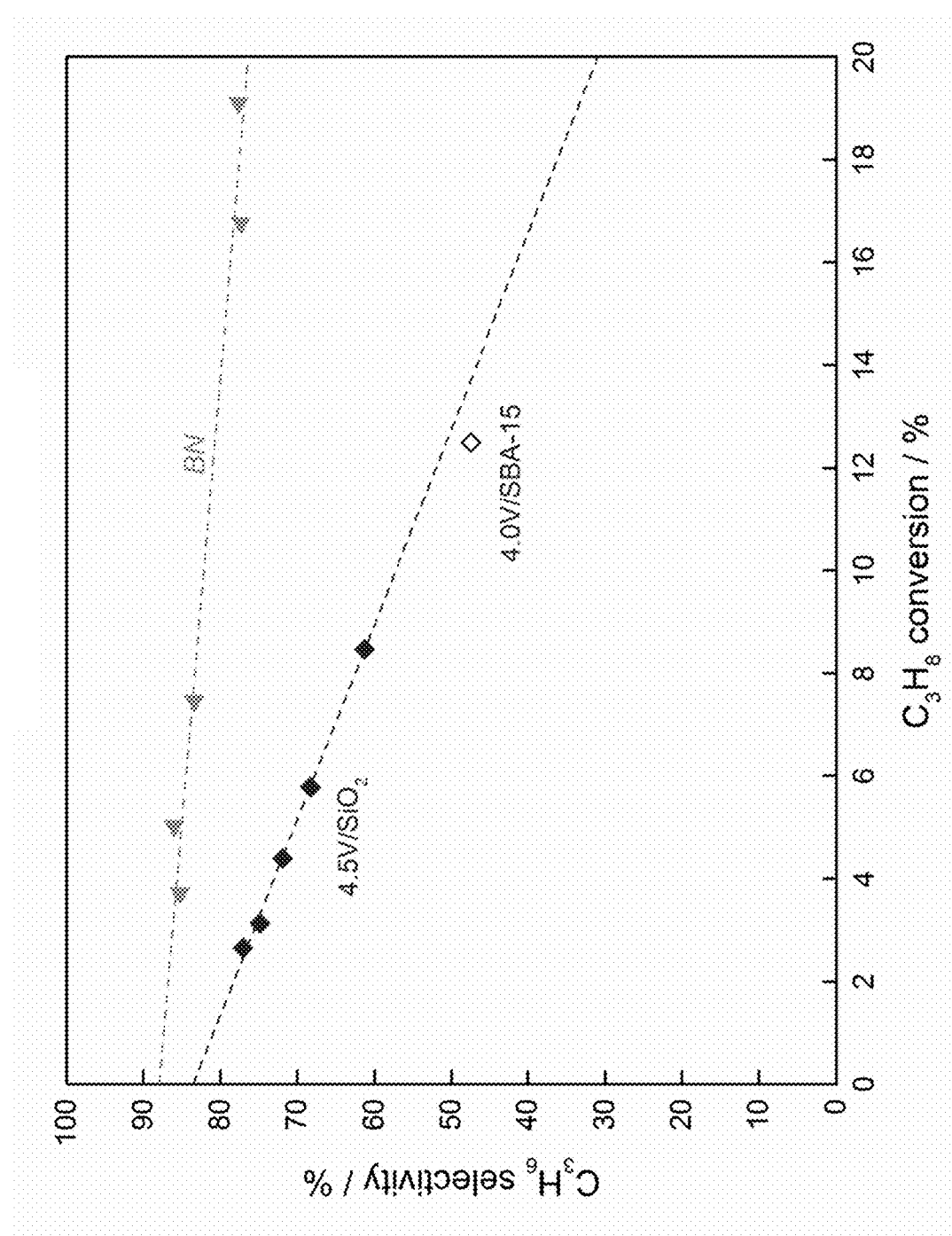
FIG. 1 is a graph showing selectivity to propene plotted against propane conversion for ODHP using boron nitride (BN) and conventional catalysts. The BN catalyst shows much more stable propene selectivity with increasing propane conversion than the more traditional vanadium oxide catalyst supported on $SiO_2$ (V/$SiO_2$) or SBA-15 (V/SBA-15).

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION

I. In General

Before the present materials and methods are described, it is understood that this invention is not limited to the particular methodology, protocols, materials, and reagents described, as these may vary. It is also to be understood that the terminology used in this disclosure is for the purpose of describing particular embodiments only, and is not intended to limit the scope of the present invention, which will be limited only by the language of the appended claims.

As used in this disclosure and in the appended claims, the singular forms "a", "an", and "the" include plural reference unless the context clearly dictates otherwise. The terms "a" (or "an"), "one or more" and "at least one" can be used interchangeably. The terms "comprising", "including", and "having" can also be used interchangeably.

Unless defined otherwise, all technical and scientific terms used in this disclosure, including element symbols, have the same meanings as commonly understood by one of ordinary skill in the art. Chemical compound names that are commonly used and recognized in the art are used interchangeably with the equivalent IUPAC name. For example, ethene is the same as ethylene, propene is the same as propylene, butene is the same as butylene, 2-methylpropane is the same as isobutane, and 2-methylpropene is the same as isobutene.

The following abbreviations are used throughout this disclosure: BN, boron nitride; BN nanomesh(es), boron nitride nanomesh(es); BNNS(s), boron nitride nanosheet(s), BNNR(s), boron nitride nanoribbon(s); BNNT(s), boron nitride nanotube(s); DH, dehydrogenation; h-BN, hexagonal form of boron nitride; OCM, oxidative coupling of methane; ODH, oxidative dehydrogenation; ODHP, oxidative dehydrogenation of propane; P, partial pressure for a given gas; S, selectivity for a given product; $WHSV^{-1}$, inverse weight-hour-space-velocity; % X, conversion for a given reactant.

All publications and patents specifically mentioned in this disclosure are incorporated by reference for all purposes, including for describing and disclosing the chemicals, instruments, statistical analysis and methodologies that are reported in the publications that might be used in connection with the disclosed methods and devices. All references cited in this disclosure are to be taken as indicative of the level of skill in the art.

II. The Invention

This disclosure is based on our discovery that the use of a boron- or nitride-containing catalyst facilitates improved oxidative dehydrogenation of alkanes, such as propane, to desired olefins, such as propene. Specifically, the disclosed methods exhibit increased selectivity towards the desired product while decreasing the production of unwanted byproducts, such as CO and $CO_2$. Furthermore, the process occurs at relatively low temperatures, and the catalyst is stable over time, and so does not need to be frequently regenerated. The catalysts can also be used for oxidative coupling of methane to produce ethane and/or ethylene.

Exemplary Forms of Boron Nitride

Boron nitride (BN) is a non-limiting example of a boron- or nitride-containing catalyst that can be used in the disclosed methods. The boron nitride catalyst can be made from any available form of boron nitride, including, without limitation, amorphous boron nitride (a-BN), hexagonal boron nitride (h-BN), cubic boron nitride (c-BN), wurtzite boron nitride (w-BN), boron nitride-containing composites, boron nitride nanotubes (BNNTs), boron nitride nanosheets (BNNSs), boron nitride nanoribbons (BNNRs) and boron nitride nanomeshes.

h-BN, a stable crystal form of BN, has a layered structure similar to graphite. Within each layer, boron and nitrogen atoms are bound by strong covalent bonds, whereas the layers are held together by weak van der Waals forces.

As shown in more detail in the examples below, we have determined that the catalytic activity of BN may be enhanced by increasing the surface area of the BN. Accordingly, forms of BN exhibiting increased surface area, such as boron nitride nanotubes and boron nitride nanomeshes, are suitable for use in the disclosed methods.

Boron nitride nanotube(s) (BNNT(s)) are cylindrical structures formed from "rolled up" sheets of alternating and covalently bonded nitrogen and boron atoms. Typical BNNTs have a diameter of several to hundreds of nanometers and a length of many micrometers. They are structurally similar to carbon nanotubes, which are made up of "rolled up" graphitic carbon sheets.

Boron nitride nanomesh(es) are two-dimensional boron nitride nanostructures consisting of a single layer of alternating and covalently bonded boron and nitrogen atoms, which self-assemble to form a highly regular mesh. The structure of BN nanomeshes is similar to the structure of graphene, in that they form an assembly of hexagonal pores. In a non-limiting example, the distance between two pore centers is 3.2 nm and the pore diameter is ~2 nm, and the pores are about 0.05 nm deep. Other terms used in the literature for this form of boron nitride include h-BN monolayers, boronitrene, white graphene, boron nitride nanosheets, boron nitride nanoribbons, and boron nitride nanoplatelets.

For more information regarding BNNTs and BN nanosheets, see, e.g., D. Golberg, Y. Bando, Y. Huang, T. Terao, M. Mitome, C. Tang and C. Zhi, *ACS Nano*, 4 (6), 2979-2993 (2010).

Oxygen Functionalization of the BN Surface

As shown in more detail in the examples below, we have determined that the catalytic activity of BN may be enhanced by functionalizing the BN surface with oxygen.

The specific method used to functionalize the BN surface with oxygen is not limited, and may include any of a number of methods known in the art. For example, Liao et al. (Liao, Y. et al., *Sci. Rep.* 5, 14510; doi: 10.1038/srep14510 (2015)), report using silver nanoparticles to oxidize h-BN, with the duration and temperatures used in the procedure affecting the atomic percentage of oxygen functionalized onto the BN surface. Many other methods are known in the art, including the nitric acid treatment used in Example 9 below.

The following examples are offered for illustrative purposes only, and are not intended to limit the scope of the invention in any way. Indeed, various modifications of the invention in addition to those shown and described herein will become apparent to those skilled in the art from the foregoing description and the following Examples and fall within the scope of the appended claims.

III. Examples

Example 1: Substantially Improved Product Selectivity for Oxidative Dehydrogenation of Propane to Propene Using the BN Catalyst In this example, we demonstrate that using a boron nitride catalyst substantially improves the selectivity of oxidative dehydrogenation of propane to propene (ODHP), particularly at higher conversions, as compared to using conventional ODHP catalysts.

Comparative ODHP Results Using Traditional Catalysts and Boron Nitride.

ODHP was performed on a gas mixture containing propane ($C_3H_8$), Oxygen ($O_2$) and nitrogen ($N_2$) flowing past the BN catalyst made up of boron nitride, a vanadium oxide catalyst supported on $SiO_2$ ($V/SiO_2$), or a vanadium oxide catalyst supported on SBA-15 (V/SBA-15). Operating conditions for both the BN and supported vanadium oxide catalysts were as follows: $P_{O2}$=0.15 atm, $P_{C3H8}$=0.3 atm, $P_{N2}$=0.55 atm, T=490° C. For BN, 200 mg of BN particles 600-710 μm in size were loaded in a 9 mm inner diameter quartz reactor with total inlet flow rates of 40-120 mL min$^{-1}$, equivalent to inverse weight-hour-space-velocity (WHSV$^{-1}$) in the range of 100-300 kg-cat s m$^{-3}$. For V/SiO$_2$, 130 mg V/SiO$_2$ particles 600-710 μm in size (along with 260 mg SiC inert diluent, equivalent in size) were loaded in a 9 mm inner diameter quartz reactor with total inlet flow rates of 60-140 mL min$^{-1}$, equivalent to WHSV$^{-1}$ in the range of 55-130 kg-cats m$^{-3}$. All carbon balances close to within ±5%. For each catalyst, inlet flowrates of the $C_3H_8/O_2/N_2$ gas mixture were varied to achieve a range of propane conversions.

Propene selectivity, S, is calculated as follows:

$$S = \frac{F_{C3H6,out}}{\sum F_{carbon\,prod}}$$

where $F_{C3H6,out}$=flow of propene out of reactor (mol s$^{-1}$ g-cat$^{-1}$)

$F_{carbon\,prod}$=flow of all carbon products out of reactor (mol s$^{-1}$ g-cat$^{-1}$)

Propane conversion, X, is calculated as follows:

$$X = \frac{\sum F_{carbon\,prod}}{F_{C3H8,in}}$$

where $F_{carbon\,prod}$=flow of all carbon products out of reactor (mol s$^{-1}$ g-cat$^{-1}$)

$F_{C3H8,in}$=flow of propane into the reactor (mol s$^{-1}$ g-cat$^{-1}$)

Inverse weight-hour-space-velocity, WHSV$^{-1}$ (kg-cat s m$^{-3}$), is calculated as follows:

$$WHSV^{-1} = \frac{M_{cat}}{F_{tot}} * 60$$

where $M_{cat}$=mass of catalyst loaded in reactor (mg)

$F_{tot}$=total flow of all inlet gasses (mL min$^{-1}$)

As seen in FIG. 1, use of the BN catalyst results in a much more stable propene selectivity with increasing propane conversion than the more traditional vanadium oxide catalyst supported on SiO$_2$ or SBA-15. Specifically, BN maintained 77% propene selectivity with 17% propane conversion, while even with a modest 13% propane conversion, the vanadium oxide catalyst supported on SBA-15 shows propene selectivity of 48%.

Figure 2:
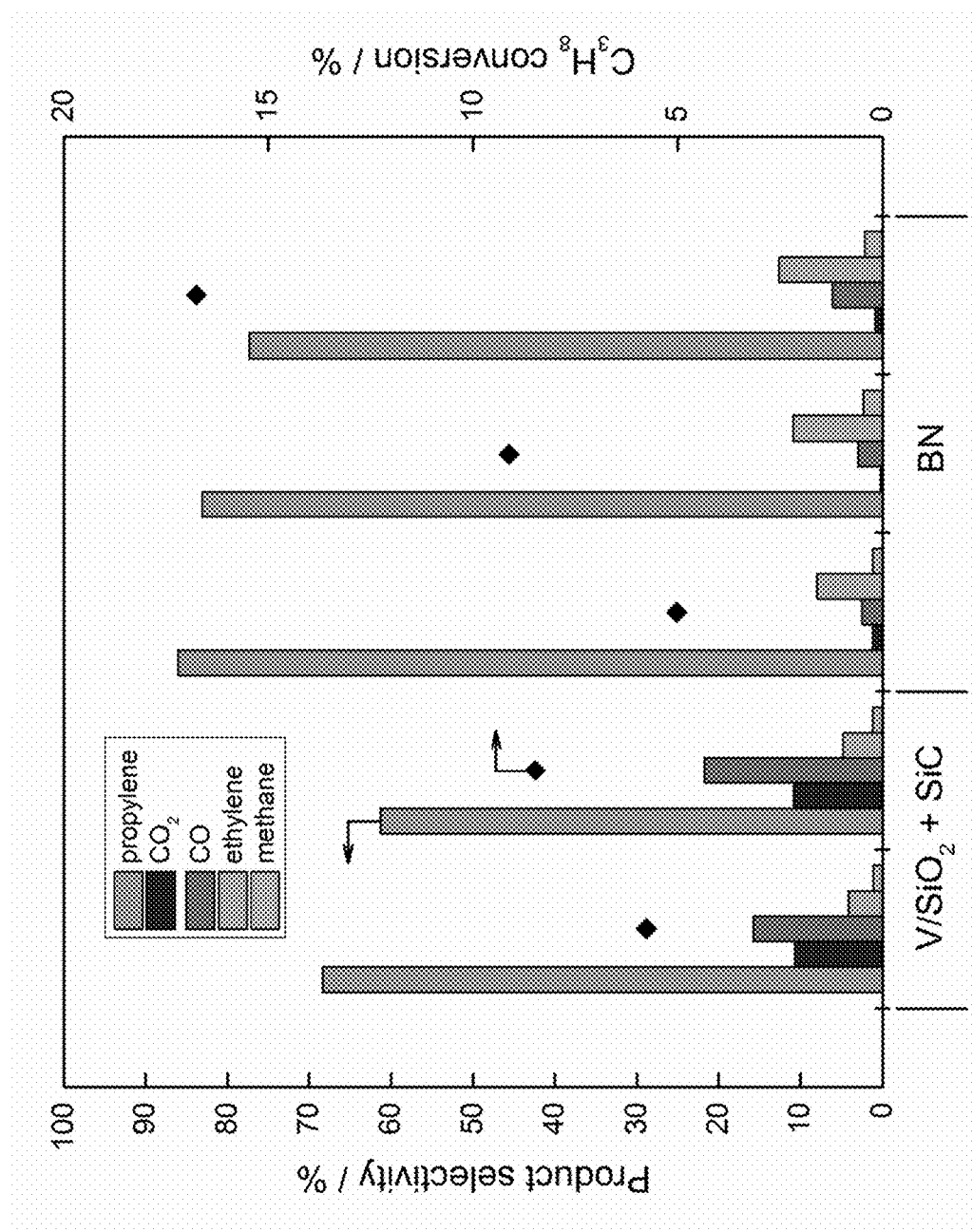
FIG. 2 is a graph showing the relationship between product selectivities and propane conversion percentages when using vanadium oxide supported on $SiO_2$ (V/$SiO_2$) or the BN catalyst. Product selectivities are represented by the bar plots and are shown on the left-axis, while propane conversions are represented by the black diamonds and are shown on the right-axis.

As seen in FIG. 2, use of the V/SiO$_2$ catalyst (diluted with inert SiC) results in a large drop in propene selectivity with only an increase of ~3% in propane conversion. In contrast, the BN catalyst shows a much more gradual drop in propene selectivity with increasing propane conversion, always showing greater selectivity to propene than the V/SiO$_2$ catalyst, even at ~17% propane conversion.

We further quantify the specific ODHP byproducts resulting from using the V/SiO$_2$+SiC and BN catalysts, and the results are shown in FIG. 2. When using the BN catalyst, the main byproduct is ethylene, an important chemical building block itself. In contrast, when using the V/SiO$_2$ catalyst, the primary byproducts are CO and CO$_2$. This indicates that BN catalyzes a drastically different mechanism of propene formation than V/SiO$_2$.

In sum, this example demonstrates that improved selectivities and byproduct mix can be obtained by using boron nitride to catalyze ODH of short chain alkanes to the corresponding olefin, in place of traditional vanadium oxide or other known catalysts.

Example 2: The BN Catalyst is Stable Over the Long Term

Figure 3:
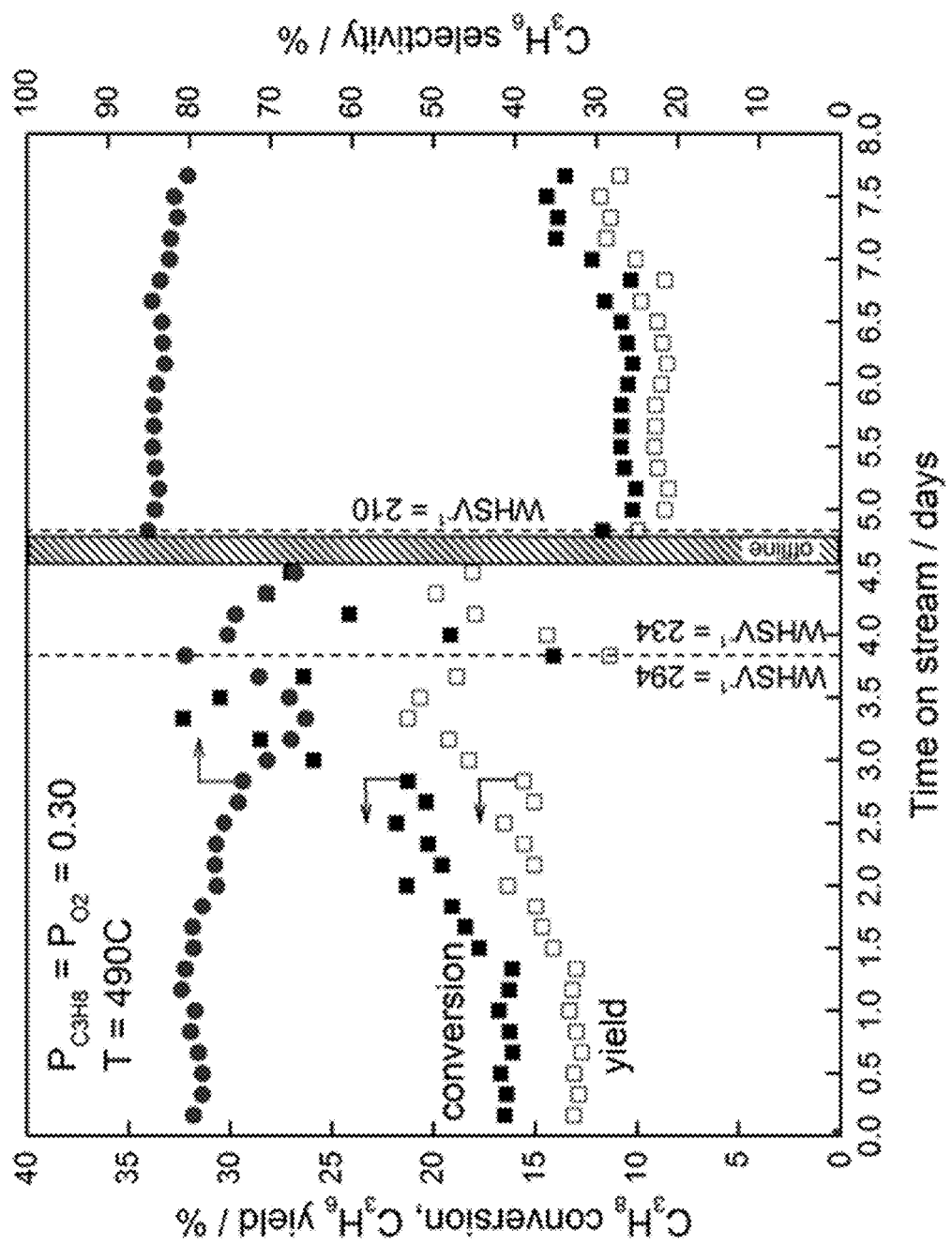
FIG. 3 is a graph showing the results of a long-term stability test completed using the BN catalyst to look for any indication of catalyst deactivation. Propane conversion and propene yield (filled-black square and open-black square, respectively) are shown on the left-axis, while propene selectivity (circle) is shown on the right-axis.

A long term stability test was completed using the BN catalyst to look for any indication of catalyst deactivation, and the results are reported in FIG. 3. Operating conditions were as follows: $P_{O2}$=0.3 atm, $P_{C3H8}$=0.3 atm, $P_{N2}$=0.4 atm, T=490° C. All carbon balances close to within ±5%. Testing proceeded for 8.0 day on stream time period.

Referring to FIG. 3, propane conversion and propene yield are shown as a function of time on stream, and the WHSV during various on stream time periods is indicated. After ~1.5 days on stream, propane conversion began to increase, along with the natural decrease in propene selectivity, indicating that the BN catalyst was becoming more active. This was likely due to the formation of additional active sites. Total inlet flowrates were then increased from 40 to 50 mL min$^{-1}$ after 4 days on stream to decrease WHSV$^{-1}$ from 294 to 234 kg-cat s m$^{-3}$, in order to bring the propane conversion back to its initial value. After an additional day, total flow rate was again increased (56 mL min$^{-1}$) to drop WHSV$^{-1}$ to 210 kg-cat s m$^{-3}$. Propane conversion again increased after several more days, suggesting the continual generation of additional active sites.

These results demonstrate that the BN catalyst is stable when used continuously for oxidative dehydrogenation over extended periods of time. Accordingly, the disclosed method is suitable for cost-efficient industrial-scale use.

Example 3: ODHP Catalyzed by Boron Nitride from Multiple Sources Demonstrates Improved Propene Selectivity, with Greater BN Surface Area Facilitating Higher Conversion Rates In this example, we demonstrate that boron nitride from two different sources catalyzed ODHP with improved selectivity for propene at relatively high conversions. Further analysis revealed that reactivity of BN for ODHP may be proportional to the surface area of the BN catalyst.

Operating conditions were as follows: $P_{O2}$=0.15 atm, $P_{C3H8}$=0.3 atm, $P_{N2}$=0.55 atm, T=490° C. 200 mg of BN particles 600-710 µm in size were loaded in a 9 mm ID quartz reactor with total inlet flow rates of 40-120 mL min$^{-1}$, equivalent to WHSV$^{-1}$ of 100-300 kg-cat s m$^{-3}$. All carbon balances close to within ±2%. Inlet flowrates of the $C_3H_8$/$O_2$/$N_2$ gas mixture were varied to achieve a range of propane conversions.

Figure 4:
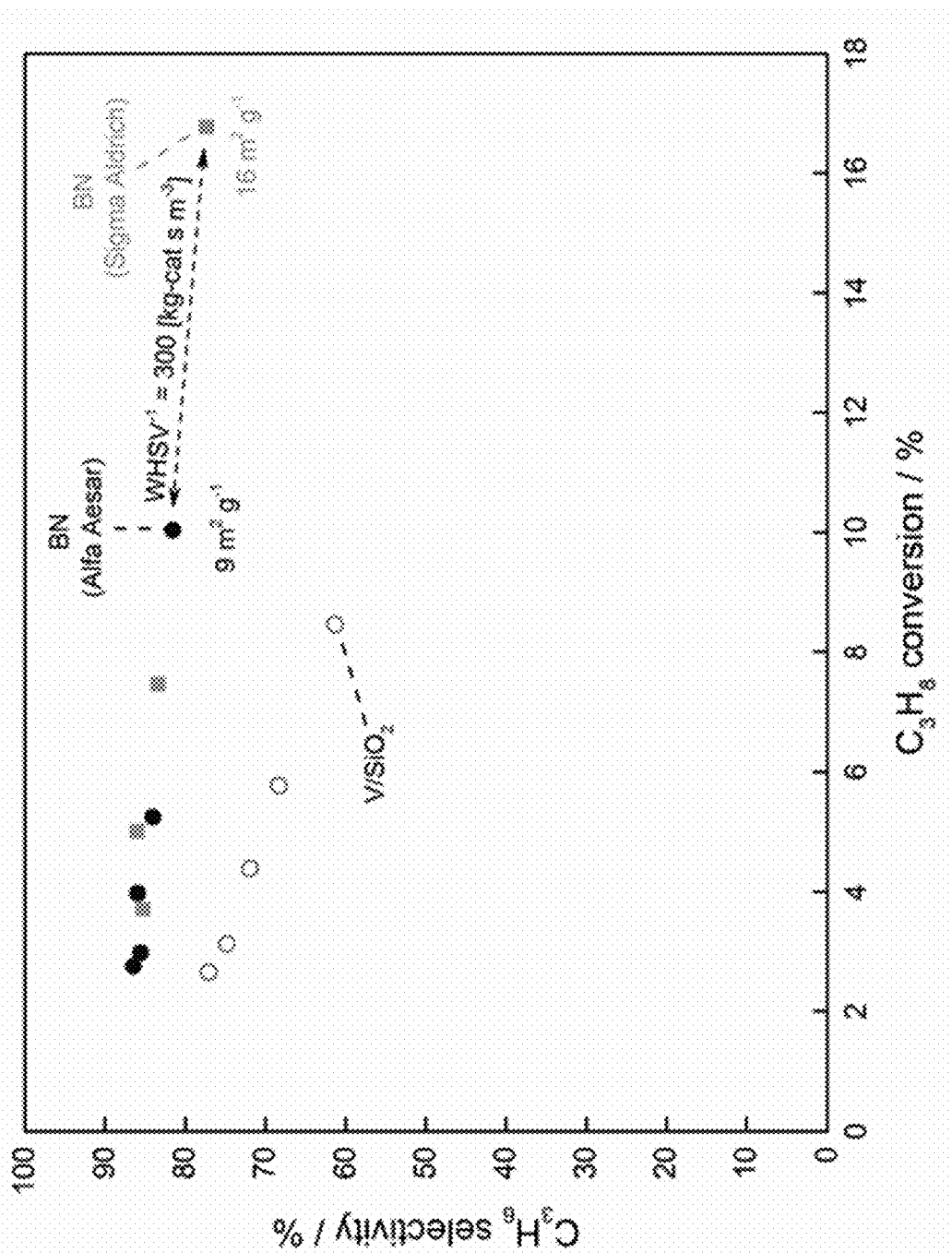
FIG. 4 is a graph showing high propene selectivity at relatively high propane conversions with the use of the BN catalyst, confirmed from BN provided by two separate chemical suppliers.

BN was used from two separate chemical suppliers: Sigma Aldrich and Alfa Aesar. As seen in FIG. 4, the results were assayed separately, and compared to the results obtained using V/SiO$_2$. Interestingly, when using identical total inlet flowrates (40 mL min$^{-1}$), equivalent to 300 kg-cat s m$^{-3}$, the BN supplied from Sigma Aldrich achieved ~17% propane conversion, while the BN supplied from Alfa Aesar only reached ~10% propane conversion. This is an indication that the BN from Sigma Aldrich is more reactive per unit of mass than that supplied by Alfa Aesar.

Analysis of the surface area of these two materials (BET) revealed that the Sigma Aldrich BN had a 1.8 times greater specific surface area than the Alfa Aesar BN. Accordingly, the reactivity of BN for oxidative propane dehydrogenation may be proportional to the BN surface area, and therefore could be improved with the synthesis of higher surface area BN materials.

Example 4: Other Boron- or Nitride-Containing Compounds are Active Catalysts for ODHP, with Boron-Containing Compounds Facilitating High Propene Selectivity and Improved Byproduct Mix In this example, we extended the ODHP catalyst assays disclosed in the previous examples using BN to a range of additional boron- and nitride-containing compounds. The results show that, in general, like BN, boron- and nitride-containing compounds can catalyze ODHP (and likely related ODH of short chain alkanes to corresponding olefins). Furthermore, the results show that in general, like BN, boron-containing compounds catalyze ODHP (and likely related ODH of short chain alkanes to corresponding olefins) with greatly improved selectivity for propene and improved byproduct mix.

Figure 5:
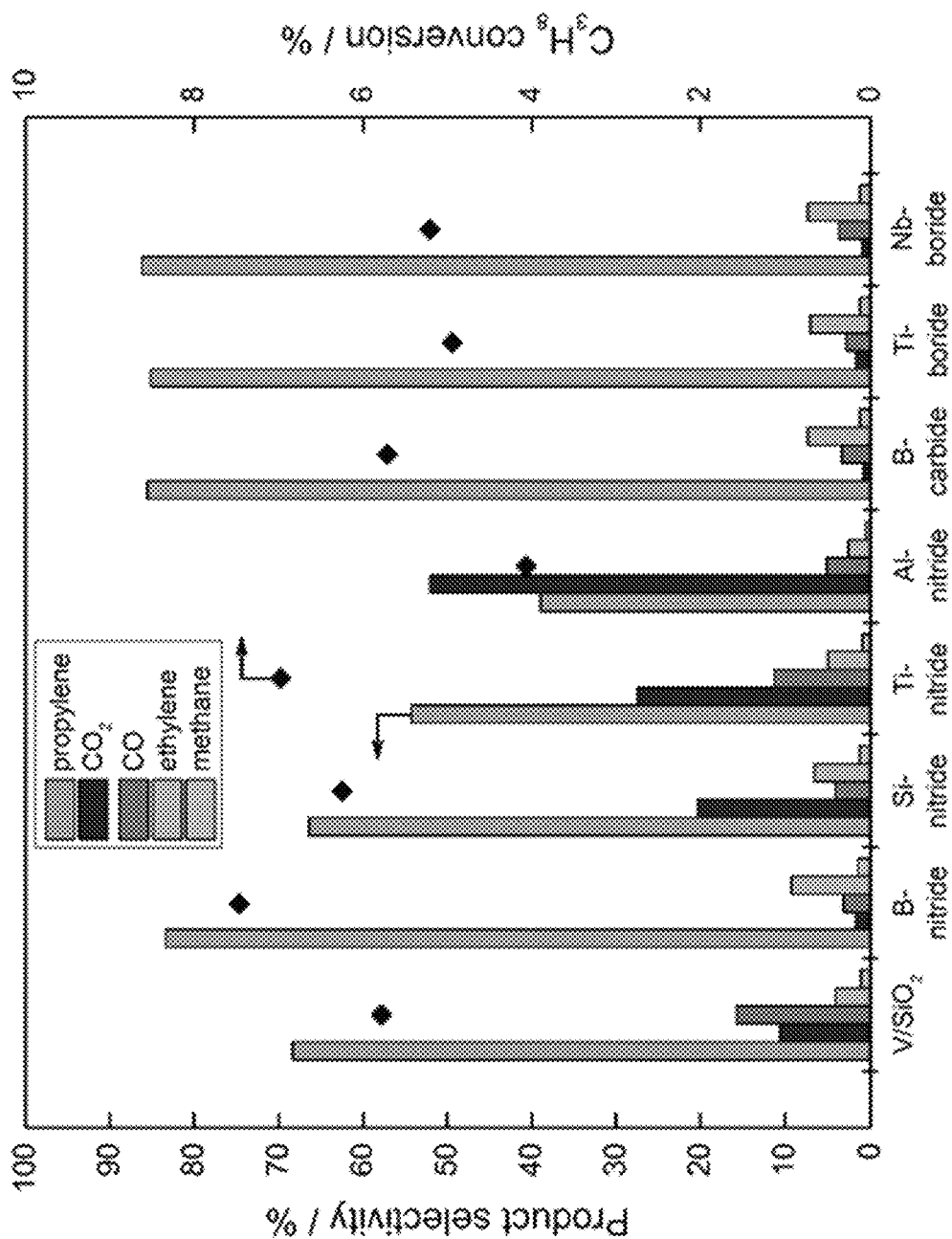
FIG. 5 is a graph showing product selectivities and propane conversion percentages using various boron- or nitride-containing catalysts that were screened for oxidative dehydrogenation of propane (ODHP). Product selectivities are represented by the bar plots and are shown on the left-axis, while propane conversion percentages are represented by the black diamonds and are shown on the right-axis.

Various boron- or nitride-containing catalysts were screened for oxidative propane dehydrogenation (ODHP), including B-nitride, Si-nitride, Ti-nitride, Al-nitride, B-carbide, Ti-boride, and Nb-boride. FIG. 5 shows product selectivities of the screened catalysts as a function of propane conversion, and also includes the corresponding data for the conventional V/SiO$_2$ catalyst. Operating conditions were as follows: $P_{O2}$=0.15 atm, $P_{C3H8}$=0.3 atm, $P_{N2}$=0.55 atm, T=490° C. Due to differences in the reactivity between catalysts, total inlet flow rates between catalysts fluctuated between 40 and 140 mL min$^{-1}$, in order to achieve ~5% propane conversion. About 200 mg of boron- or nitride-containing catalysts 600-710 µm in size were loaded in a 9 mm inner diameter quartz reactor. All carbon balances close to within ±2%.

As seen in FIG. 5, all the tested boron- or nitride-containing catalysts show activity for ODHP. Furthermore, all the tested boron-containing catalysts (B-nitride, B-carbide, Ti-boride, Nb-boride) display high selectivity to propene, with the primary byproduct being ethylene. In contrast, nitride-containing catalysts other than BN (Si-, Ti, Al-nitride) show markedly lower selectivity to propene than the boron-containing alternatives, and produce CO$_2$ and CO as the primary byproducts.

Inlet flowrates of the $C_3H_8$/$O_2$/$N_2$ gas mixture past the screened boron-containing, nitride-containing and V/SiO$_2$ catalysts were then varied to achieve a range of propane conversions. Operating conditions were as follows: $P_{O2}$=0.15 atm, $P_{C3H8}$=0.3 atm, $P_{N2}$=0.55 atm, T=490° C. About 200 mg of boron- or nitride-containing catalysts 600-710 µm in size were loaded in a 9 mm inner diameter quartz reactor with total inlet flowrates of 40-140 mL min$^{-1}$, equivalent to WHSV$^{-1}$ of 100-300 kg-cat s m$^{-3}$. All carbon balances close to within ±5%.

Figure 6:
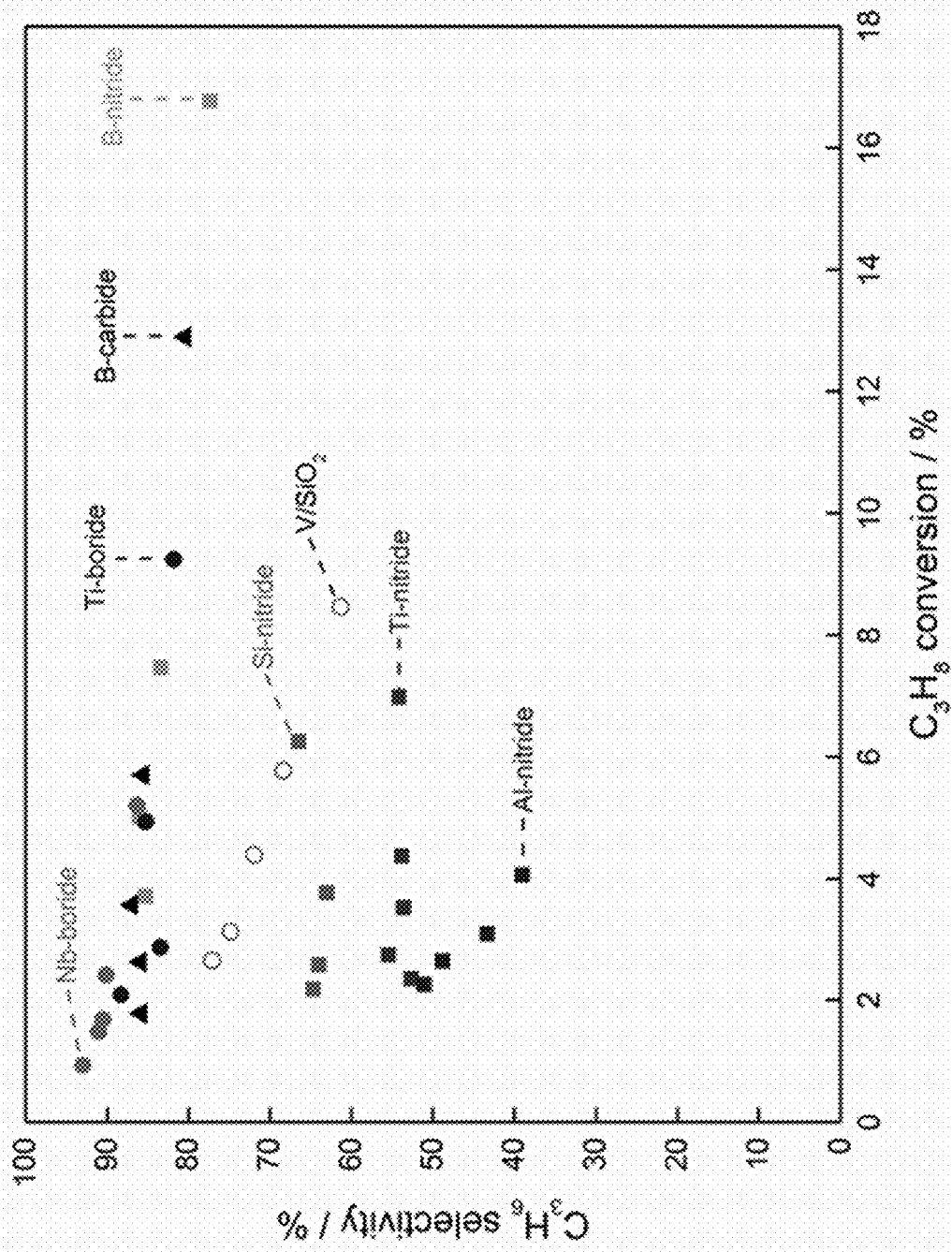
FIG. 6 is a graph showing selectivity to propene plotted against propane conversion for ODHP using a variety of catalysts. Both boron- and nitride-containing catalysts show activity for ODHP.

As shown in FIG. 6, the boron-containing catalysts maintained high propene selectivity even at high propane conversions. Nitride-containing catalysts showed lower selectivity to propene, but in the case of Si- and Ti-nitride, propene selectivity did not decrease with increasing propane conversion.

In sum, this example demonstrates that a variety of boron- and nitride-containing catalyst can be used to catalyze the oxidative dehydrogenation of short chain alkanes to corresponding olefins.

Example 5: Selective Oxidative Dehydrogenation of Propane to Propene Using Boron Nitride Catalysts In this example, we extend the BN ODH catalyst results disclosed in the previous examples in several specific ways, while providing additional details. First, we demonstrate that effective ODH catalysts can be made from either of two different forms of boron nitride: hexagonal boron nitride (h-BN) or boron nitride nanotubes (BNNTs). BNNT catalysts promote increased propene productivity as compared to h-BN catalysts. Second, we propose a mechanism of action that is consistent with our data that is fundamentally different from the mechanism of action for ODH using traditional catalysts, such as supported vanadia.

Summary

The exothermic reaction of propane with oxygen to generate propene and water has the potential to be a game-changing technology in the chemical industry. However, even after decades of research, the selectivity to propene remains too low to make the reaction economically attractive. This notoriously low selectivity is due to a fundamental scientific challenge: the desired olefin is much more reactive than the alkane substrate, and is therefore readily oxidized to thermodynamically favored $CO_2$.

In this example we report that hexagonal boron nitride (h-BN) and boron nitride nanotubes (BNNTs) have unique catalytic properties and facilitate an unprecedented selectivity to propene. As an example, at 14% propane conversion, we obtain a selectivity of 77% towards propene and 13% towards ethene, another desired alkene. Based on catalytic experiments, in conjunction with spectroscopic investigations and ab initio modeling, we put forward a mechanistic hypothesis in which oxygen-terminated armchair BN edges are proposed to be the catalytic active sites.

Experiments, Results, and Discussion

Here, we present both hexagonal boron nitride (h-BN) and boron nitride nanotubes (BNNTs) as metal-free materials able to catalyze the ODHP reaction. While graphene and fullerene materials are emerging as catalysts for partial alkane oxidations (D. R. Dreyer, H. P. Jia, C. W. Bielawski, *Angew. Chem.*, 122, 6965-6968 (2010); J. Zhang, X. Liu, R. Blume, A. Zhang, R. Schlogl, D. S. Su, *Science*, 322, 73-77 (2008); B. Frank, J. Zhang, R. Blume, R. Schogl, D. S. Su, *Angew. Chem. Int. Ed.*, 48, 6913-6917 (2009)), BN materials, one of the "inorganic analogues" of graphene, have yet to be explored in the art for their own catalytic activity. It is actually remarkable that BN, a material deemed to be very stable and inert, is catalytically active at all.

A supported vanadia on silica catalyst ($V/SiO_2$) was used in this work to make direct comparisons to the catalytic performance of BN. These materials were loaded into a quartz tube reactor heated to 460-500° C. under flowing propane, oxygen and nitrogen as an inert carrier gas. Reaction parameters such as temperature, catalyst mass, total gas flow-rate, and partial pressures of propane ($P_{C3H8}$) and oxygen ($PO_2$) were varied to observe changes to product distributions by sampling the reactor exhaust stream via online gas chromatography and mass spectrometry. Gas contact time with the catalyst is represented in this work as the inverse-weight-hour-space-velocity ($WHSV^{-1}$, [kg-catalyst s mol $C_3H_8^{-1}$]), which was varied primarily by altering the total gas flow-rate.

Figure 7A:
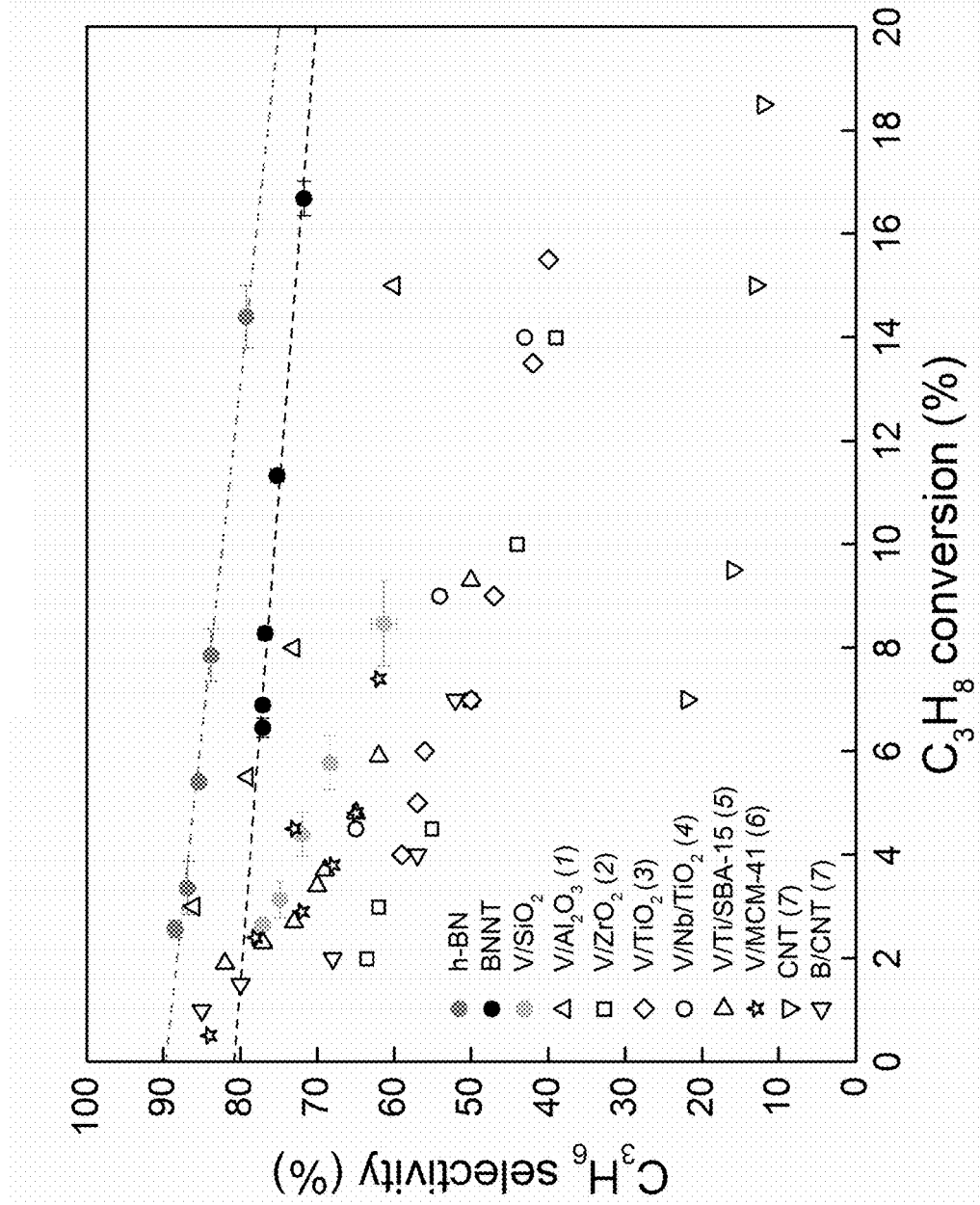
FIG. 7A is a graph showing selectivity to propene plotted against propane conversion for ODHP, comparing previously reported data from representative catalysts to hexagonal boron nitride (h-BN) and boron nitride nanotubes (BNNT). Open shapes indicate data from other works, cited within the FIG. 1-7; 1: B. Frank, A. Dinse, O. Ovsitser, E. V. Kondratenko, R. Schomaecker, *Appl. Catal. A: Gen.*, 323, 66-76 (2007); 2: C. L. Pieck, M. A. Banares, J. L. G. Fierro, *J. Catal.*, 224, 1-7 (2004); 3: A. Christodoulakis, M. Machli, A. A. Lemonidou, S. Boghosian, *J. Catal.*, 222, 293-306 (2004); 4: P. Viparelli, P. Ciambelli, L. Lisi, G. Ruoppolo, G. Russo, J. C. Volta, *Appl. Catal. A: Gen.*, 184, 291-301 (1999); 5: C. Carrero, M. Kauer, A. Dinse, T. Wolfram, N. Hamilton, A. Trunschke, R. Schlogl, R. Schomaecker, *Catal. Sci. Technol.*, 4, 786-794 (2014); 6: E. V. Kondratenko, M. Cherian, M. Baerns, D. Su, R. Schlogl, X. Wang, I. E. Wachs, *J. Catal.*, 234, 131-142 (2005); 7: B. Frank, J. Zhang, R. Blume, R. Schogl, D. S. Su, *Angew. Chem. Int. Ed.*, 48, 6913-6917 (2009)). Gas contact times (WHSV$^{-1}$) are varied to achieve a range of conversions and differs depending on the reactivity of the material; V/SiO$_2$: 5-15 kg-cat s mol C$_3$H$_8$$^{-1}$; h-BN: 15-40; BNNT: 2-5; T=490° C., P$_{O2}$=0.15 atm, P$_{C3H8}$=0.3 atm.

Use of BN materials results in extraordinary selectivity to propene not observed before under ODHP conditions. For instance, h-BN afforded 77% selectivity to propene at 14% propane conversion (FIG. 7A). Meanwhile, the traditional $V/SiO_2$ allows for a modest 61% propene selectivity at only 9% propane conversion (J. T. Grant, C. A. Carrero, A. M. Love, R. Verel, I. Hermans, *ACS Catal.*, 5, 5787-5793 (2015)). The obtained selectivities using state-of-the-art ODHP catalysts (1-7; 1: B. Frank, A. Dinse, O. Ovsitser, E. V. Kondratenko, R. Schomaecker, *Appl. Catal. A: Gen.*, 323, 66-76 (2007); 2: C. L. Pieck, M. A. Banares, J. L. G. Fierro, *J. Catal.*, 224, 1-7 (2004); 3: A. Christodoulakis, M. Machli, A. A. Lemonidou, S. Boghosian, *J. Catal.*, 222, 293-306 (2004); 4: P. Viparelli, P. Ciambelli, L. Lisi, G. Ruoppolo, G. Russo, J. C. Volta, *Appl. Catal. A: Gen.*, 184, 291-301 (1999); 5: C. Carrero, M. Kauer, A. Dinse, T. Wolfram, N. Hamilton, A. Trunschke, R. Schlogl, R. Schomaecker, *Catal. Sci. Technol.*, 4, 786-794 (2014); 6: E. V. Kondratenko, M. Cherian, M. Baerns, D. Su, R. Schlogl, X. Wang, I. E. Wachs, *J. Catal.*, 234, 131-142 (2005); 7: B. Frank, J. Zhang, R. Blume, R. Schogl, D. S. Su, *Angew. Chem. Int. Ed.*, 48, 6913-6917 (2009)) are compared in FIG. 7A. The decrease in propene selectivity with increasing propane conversion is indicative of the facile over-oxidation of propene to $CO_x$.

Figure 7B:
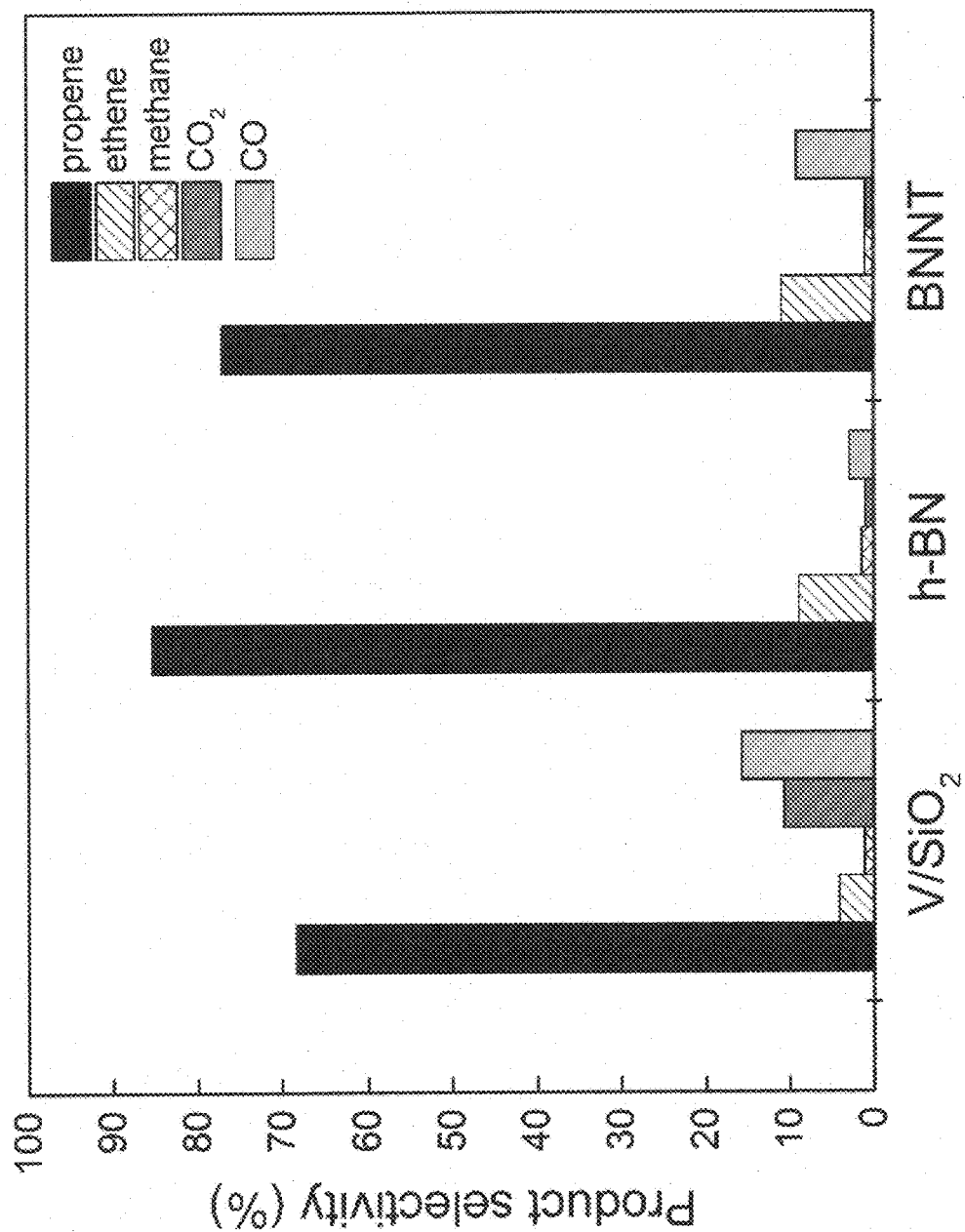
FIG. 7B is a bar graph showing comparisons of ODHP product selectivity among V/SiO$_2$ (X$_{C3H8}$=5.8%), h-BN (X$_{C3H8}$=5.4%) and BNNT (X$_{C3H8}$=6.5%) catalysts. Product selectivity is represented by shaded bars. Gas contact times (WHSV$^{-1}$) are varied to achieve a range of conversions and differs depending on the reactivity of the material; V/SiO$_2$: 5-15 kg-cat s mol C$_3$H$_8$$^{-1}$; h-BN: 15-40; BNNT: 2-5; T=490° C., P$_{O2}$=0.15 atm, P$_{C3H8}$=0.3 atm.
Figure 8:
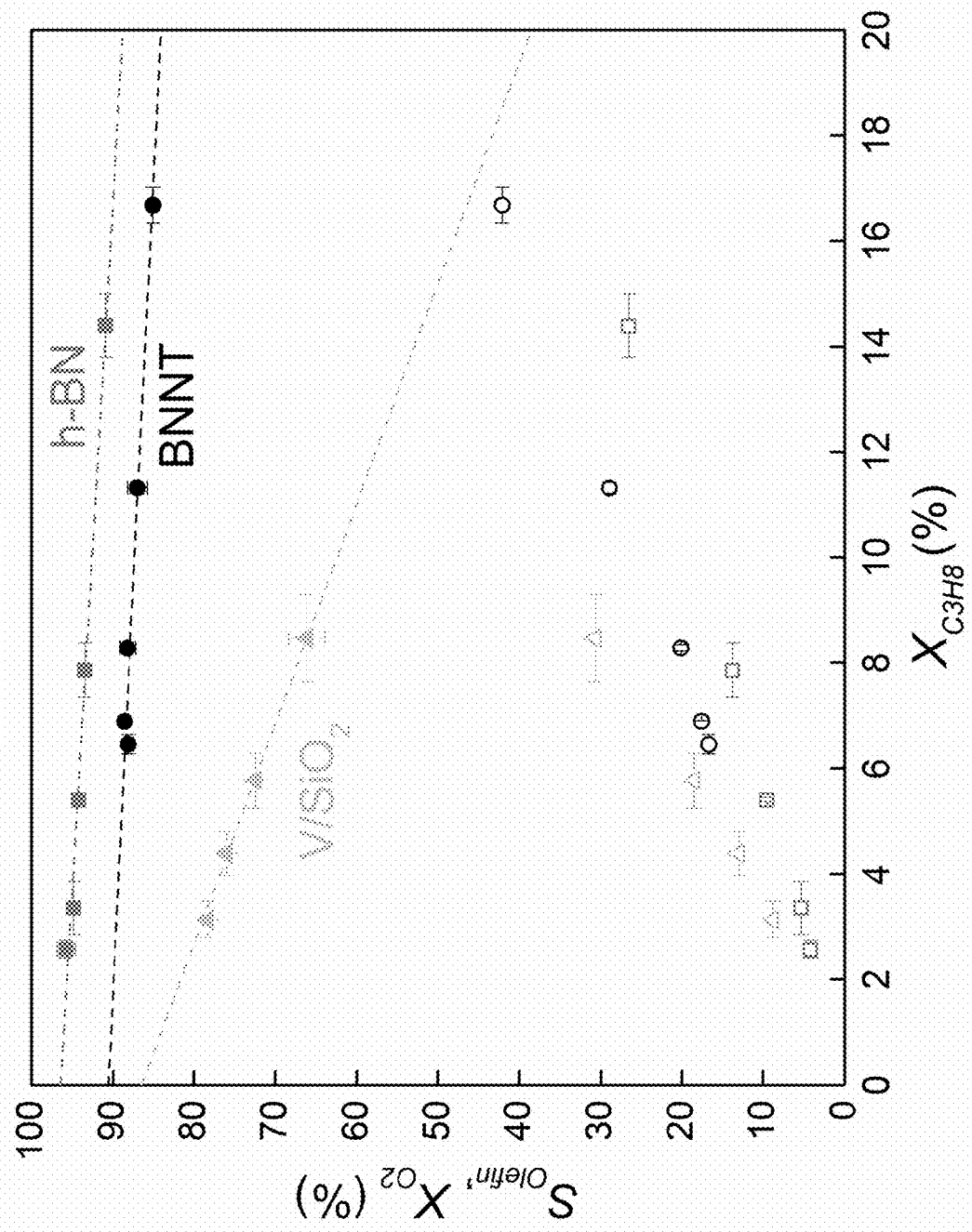
FIG. 8 is a graph showing ODHP selectivity to olefins (propene+ethene) (filled shapes), as well as oxygen conversion (open shapes), plotted against propane conversion, comparing hexagonal boron nitride (h-BN, square shapes) and boron nitride nanotubes (BNNT, circular shapes). Use of BN materials results in higher olefin selectivity and lower consecutive propene over-oxidation (corresponding to the slope of these curves) than when using V/SiO$_2$. Oxygen remains present even at high propane conversion. Gas contact time with these catalysts varies depending on the reactivity of the material; h-BN: 15-40 (kg-cat s mol C$_3$H$_8$$^{-1}$); V/SiO$_2$: 5-15 (kg-cats mol C$_3$H$_8$$^{-1}$); BNNT: 2-5 (kg-cats mol C$_3$H$_8$$^{-1}$); T=490° C., P$_{O2}$=0.15 atm, P$_{C3H8}$=0.3 atm (balance N$_2$).
Figure 9:
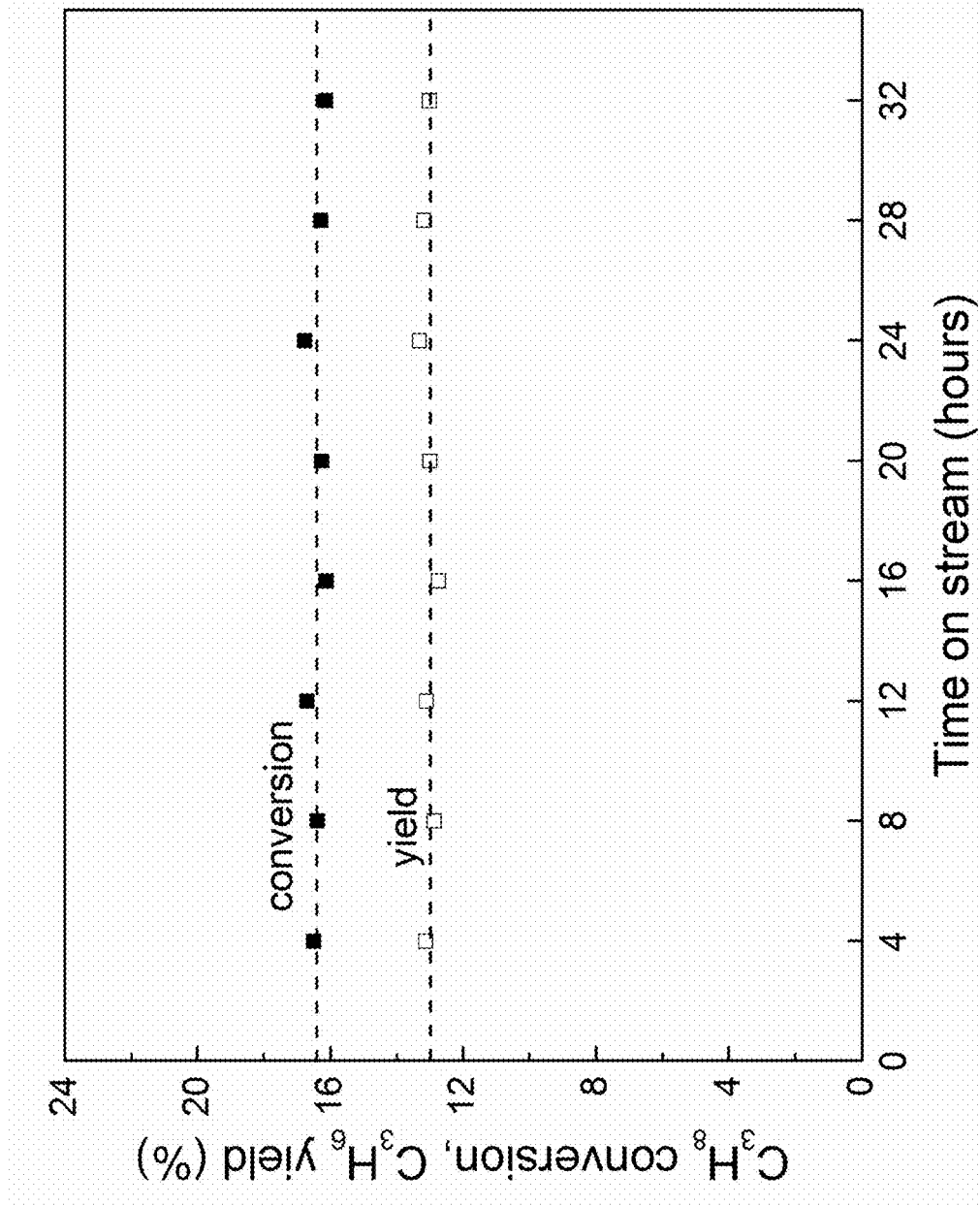
FIG. 9 is a graph showing ODHP propane conversion and propene yield as a function of time on stream using h-BN. Propane conversion (filled shapes) and propene yield (open shapes) remain stable for at least 32 hours on stream when the experiment was discontinued. T=490° C., WHSV$^{-1}$=24 kg-cat s mol C$_3$H$_8$$^{-1}$, P$_{O2}$=0.2 atm, P$_{C3H8}$=0.3 atm (balance N$_2$).

The entire product distribution further distinguishes boron nitride materials from supported vanadia catalysts (FIG. 7B). When using the supported vanadia catalyst the main byproducts are COx, accounting for 33% of total product selectivity at 9% propane conversion. Conversely, when using BN materials, the main byproduct is ethene, a highly valuable olefin itself, rather than COx. The combined propene and ethene selectivity is 90% at 14% propane conversion using h-BN (FIG. 8). We furthermore verified that the catalytic activity of the BN material remains stable for at least 32 hours on stream (FIG. 9), validating the catalyst stability.

Figure 7C:
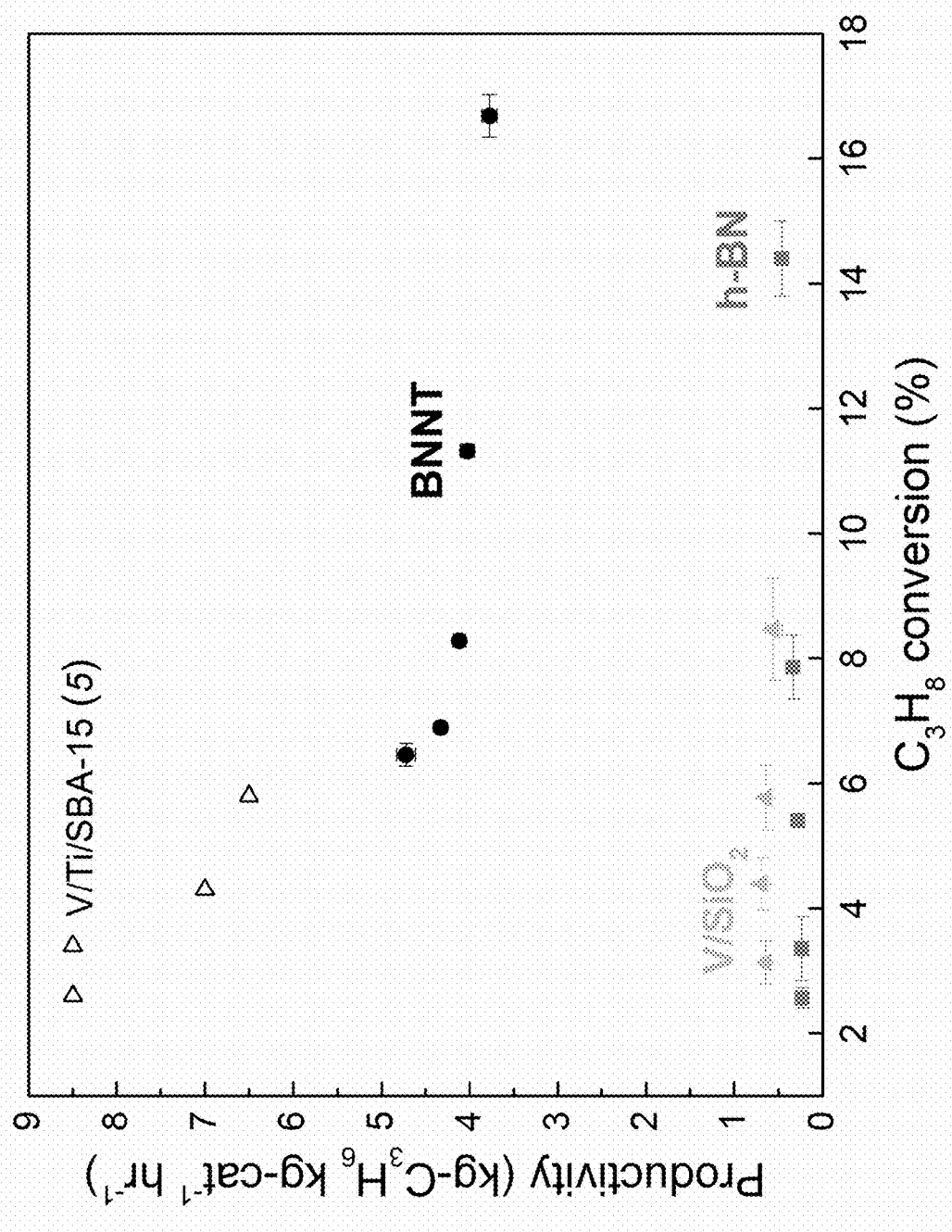
FIG. 7C is a graph showing comparisons of ODHP propene productivity (kg-C$_3$H$_6$ kg-cat$^{-1}$ hr$^{-1}$) plotted as a function of C$_3$H$_8$ conversion among V/SiO$_2$, h-BN and BNNT catalysts. The great selectivity to propene afforded by BN materials, coupled with the increased activity of BNNT, leads to superior productivity using BNNT. Gas contact times (WHSV$^{-1}$) are varied to achieve a range of conversions and differs depending on the reactivity of the material; V/SiO$_2$: 5-15 kg-cats mol C$_3$H$_8$$^{-1}$; h-BN: 15-40; BNNT: 2-5; T=490° C., P$_{O2}$=0.15 atm, P$_{C3H8}$=0.3 atm.
Figure 10:
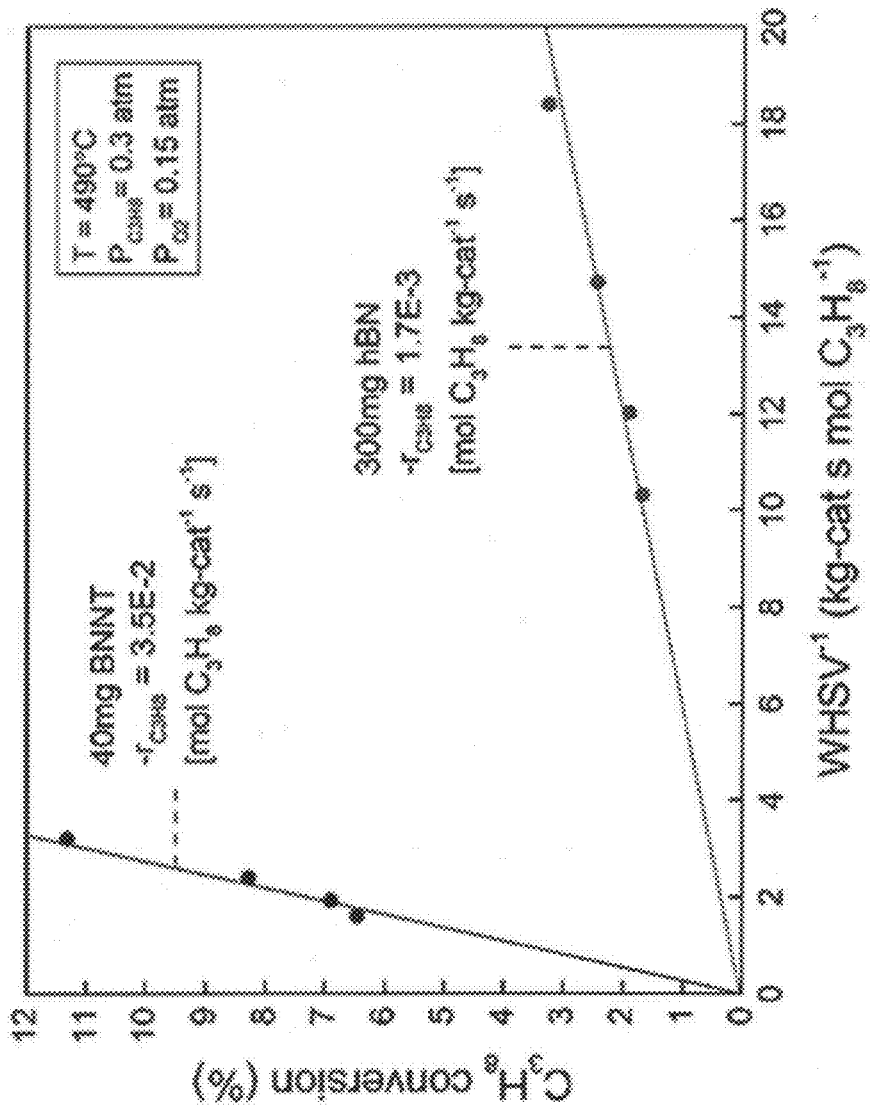
FIG. 10 is a graph showing ODHP propane conversion plotted as a function of inverse-weight-hour-space-velocity (WHSV$^{-1}$, kg-cat s mol-C$_3$H$_8$$^{-1}$), comparing h-BN (lower right line) to BNNT (upper left line) catalysts. The slope of each of these lines indicates the rate of propane consumption. Much less BNNT is needed to achieve equivalent conversions when using h-BN as a consequence of the superior reactivity of the BNNT material. T=490° C., P$_{O2}$=0.15 atm, P$_{C3H8}$=0.3 atm (balance N$_2$).

The analogous product distributions for both h-BN and BNNTs suggest a similar reaction mechanism for these BN materials. However, BNNTs exhibit a rate of propane consumption [mol $C_3H_8$ kg-$cat^{-1}$ $s^{-1}$] more than one order-of-magnitude higher than observed with h-BN (FIG. 10). The higher activity of BNNTs at least partially reflects the higher surface area of BNNTs relative to h-BN (BNNT: 97±5 $m^2$ $g^{-1}$ versus h-BN: 16±1 $m^2$ $g^{-1}$) (J. Kibsgaard, Z. Chen, B. N. Reinecke, T. F. Jaramillo, *Nat. Mater.*, 11, 963-969 (2012)); however, the rate of propane consumption is more than three times higher with BNNT than with h-BN when normalized for surface area (BNNT: $3.6 \times 10^{-7}$ mol $C_3H_8$ $s^{-1}$ $m^{-2}$ versus h-BN: $1.1 \times 10^{-7}$ mol $C_3H_8$ $s^{-1}$ $m^{-2}$). This high reactivity and selectivity with BNNTs results in a substantial enhancement in the observed propene productivity [kg-$C_3H_6$ kg-$cat^{-1}$ $hr^{-1}$] (FIG. 7C), comparable to values deemed attractive for commercial implementation of this "on-purpose" propene technology (C. Carrero, M. Kauer, A. Dinse, T. Wolfram, N. Hamilton, A. Trunschke, R. Schlogl, R. Schomaecker, *Catal. Sci. Technol.*, 4, 786-794 (2014); F. Cavani, N. Ballarini, A. Cericola, *Catal. Today*, 127, 113-131 (2007)).

Figure 11A:
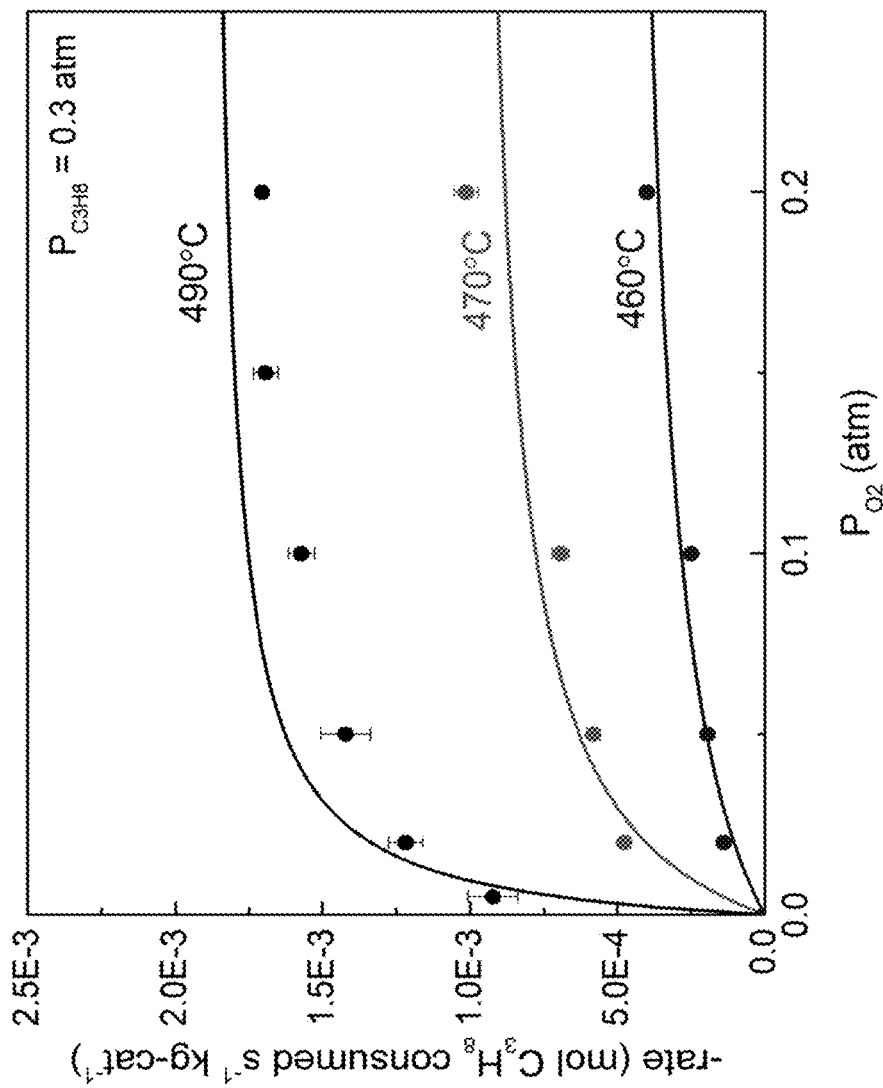
FIGS. 11A and 11B are graphs showing rates of ODHP propane consumption using h-BN as a function of (11A) P$_{O2}$ (P$_{C3H8}$ constant at 0.3 atm), and (B) P$_{C3H8}$ (P$_{O2}$ constant at 0.2 atm) fit with Eley-Rideal kinetics, showing O$_2$ adsorption and second-order dependence with respect to P$_{C3H8}$. Solid lines are a least-square fit taking into account all experimental data points at each respective temperature using the rate law displayed in FIG. 11B.
Figure 11B:
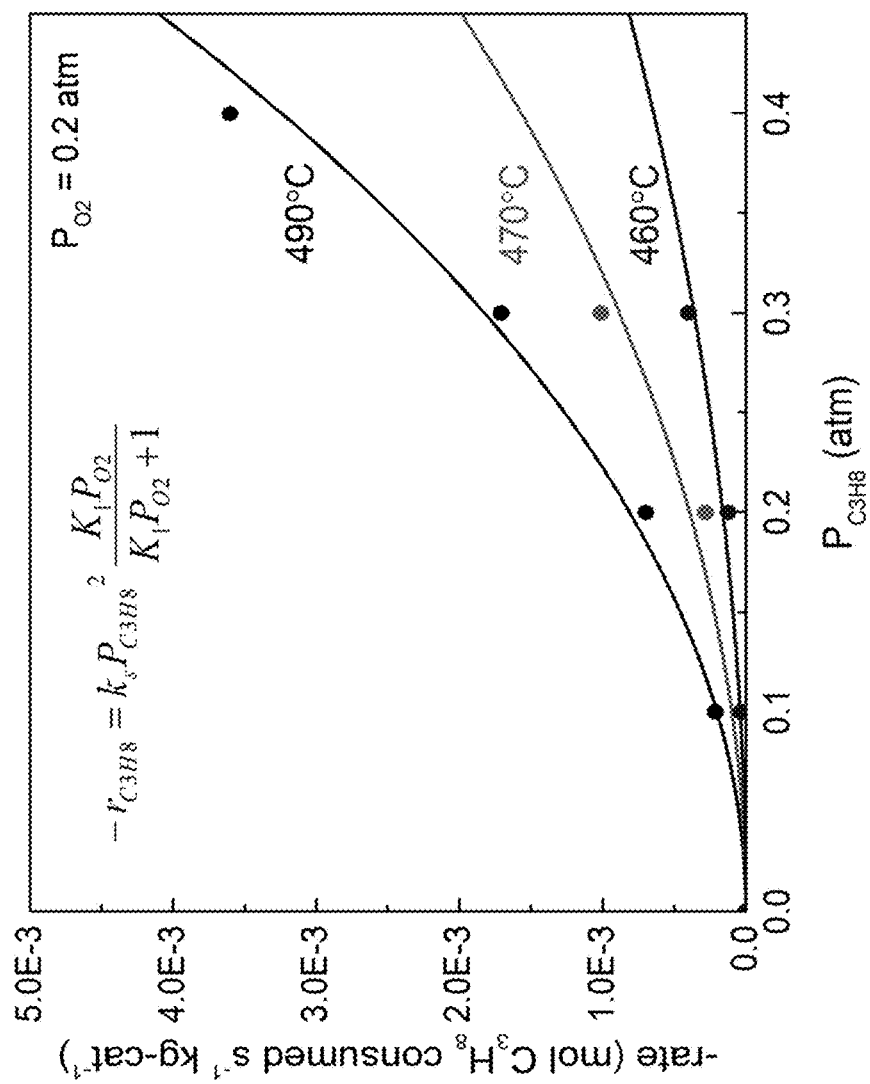

Further kinetic insights were obtained by studying the influence of reactant concentrations ($PO_2$, $P_{C3H8}$) on the reaction rate. The inclusion of oxygen as a reactant is required for propane conversion using BN materials. The rate of propane consumption using h-BN indicates oxygen activation on the BN surface (FIG. 11A) and second-order dependence with respect to $P_{C3H8}$ (FIG. 11B). This kinetic behavior clearly distinguishes boron nitride from traditional supported vanadia catalysts, which follow a Mars van Krevelen mechanism (rate-determining substrate oxidation, followed by fast re-oxidation of the surface by oxygen) that typically leads to zero-order rate dependence with respect to $P_{O2}$ and first order in propane (K. Chen, A. Khodakov, J. Yang, A. T. Bell, E. Iglesia, *J. Catal.*, 186, 325-333 (1999)).

It is surprising that BN, a material known for its high stability under oxidative conditions (Z. Liu, Y. Gong, W. Zhou, L. Ma, J. Yu, J. C. Idrobo, J. Jung, A. H. MacDonald, R. Vajtai, J. Lou, P. M. Ajayan, *Nat. Commun.*, 4, 2541 (2013); Y. Chen, J. Zou, S. J. Campbell, G. L. Caer, *Appl. Phys. Lett.*, 84, 2430-2432 (2004)), is catalytically active at all. So far it has been explored for its unique electronic, thermoelectric and mechanical properties (Y. Lin, J. W.

Figure 12:
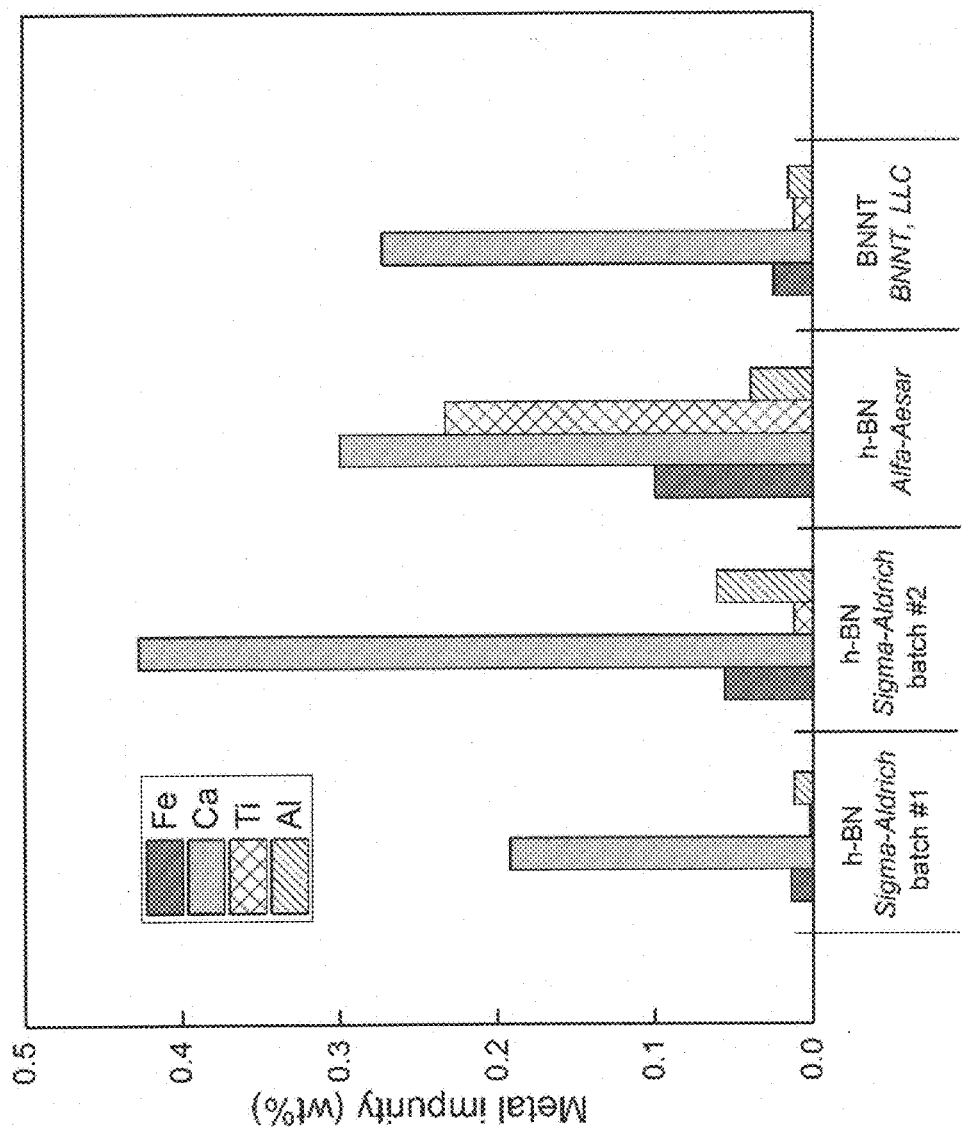
FIG. 12 is a bar graph showing metal impurity analysis of BN materials from various suppliers (Sigma-Aldrich, Alfa-Aesar, and BNNT, LLC), as well as two batches from Sigma-Aldrich (batch #1: Lot STBF0279V; batch #2: Lot STBF7843V). Additional metals (Ni, Pt, V, Cu, Zr, Ga, Mo, Ag, and Na) were screened, but always registered below the detection limit.
Figure 13:
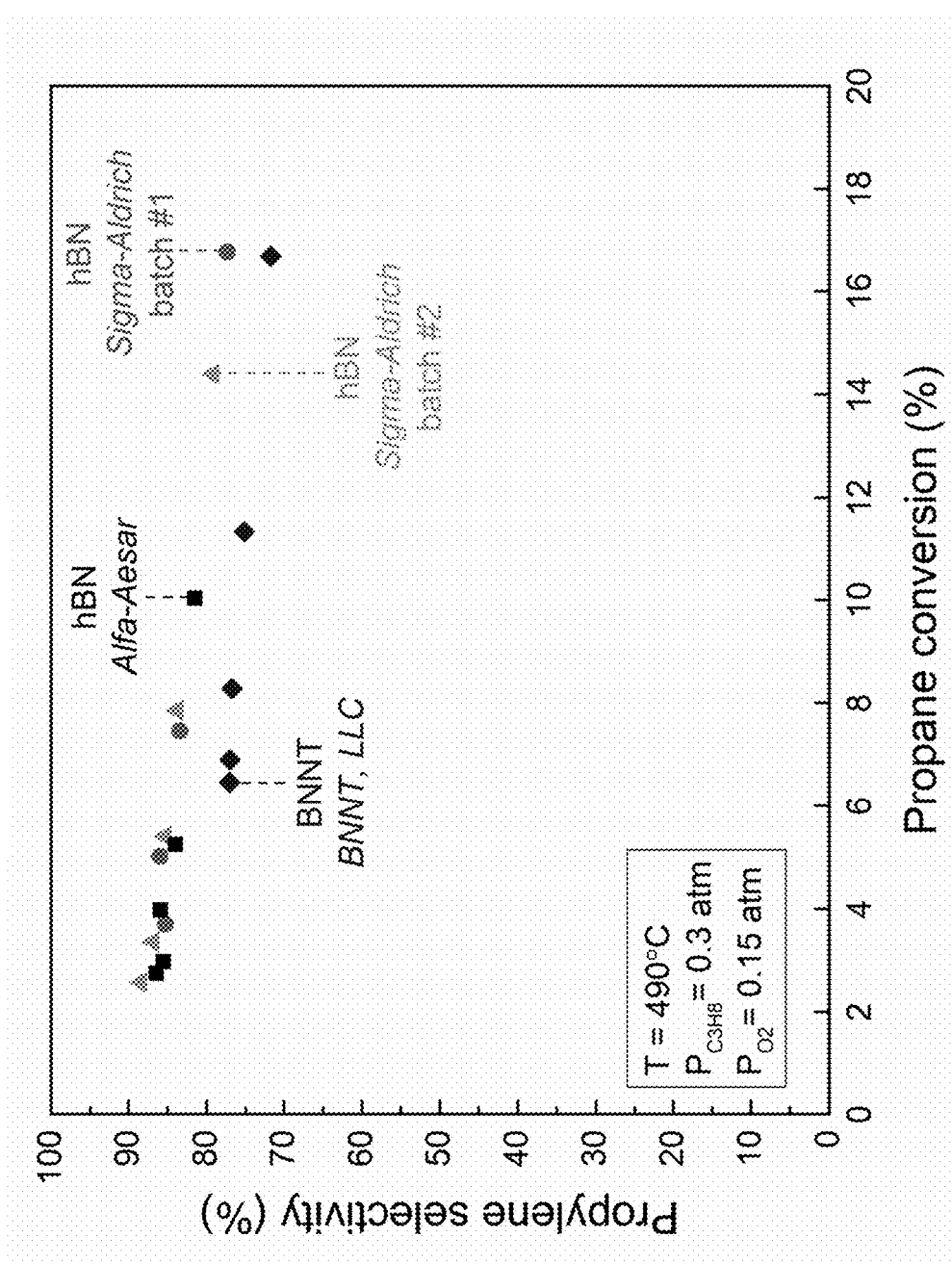
FIG. 13 is a graph showing ODHP propene selectivity plotted as a function of propane conversion for h-BN supplied by Alfa-Aesar and Sigma-Aldrich (batch #1: Lot STBF0279V, circles; batch #2: Lot STBF7843V, triangles) and BNNT (BNNT, LLC, diamonds). Despite slight differences in metal impurities between batches and suppliers, selectivity to propene between samples is almost identical (±5%). WHSV$^{-1}$: 15-40 (kg-cat s mol C$_3$H$_8$$^{-1}$) [h-BN]; 2-5 (kg-cat s mol C$_3$H$_8$$^{-1}$) [BNNT]; T=490° C., P$_{O2}$=0.15 atm, P$_{C3H8}$=0.3 atm (balance N$_2$).
Figure 14:
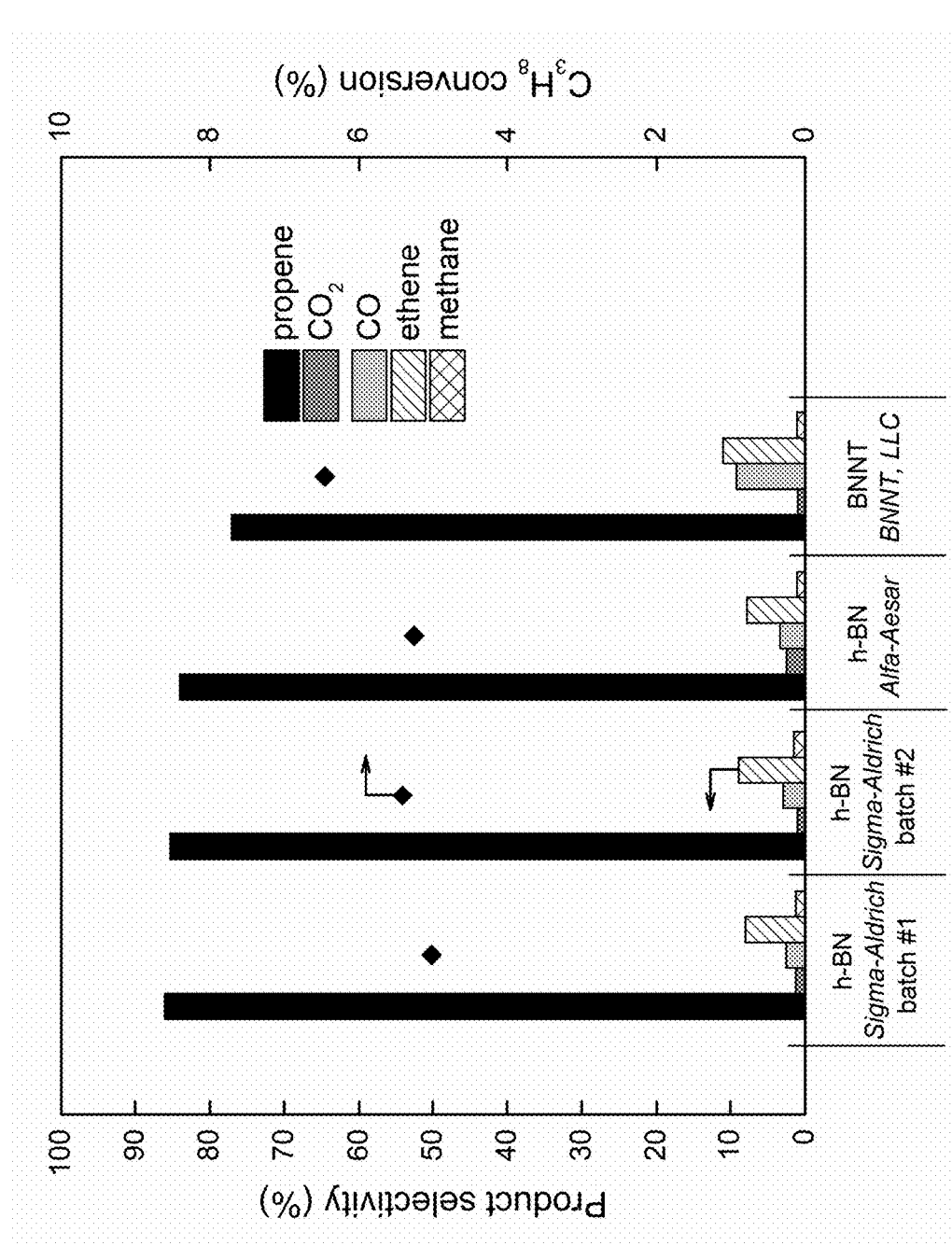
FIG. 14 is a bar graph showing comparisons of ODHP propane conversion (diamonds, right-axis) and product selectivity (bars, left-axis) among different BN suppliers (Sigma-Aldrich, Alfa-Aesar, and BNNT, LLC) and batches of h-BN from Sigma-Aldrich (batch #1: Lot STBF0279V; batch #2: Lot STBF7843V). Despite slight differences in metal impurities between batches and suppliers, product selectivity between samples are almost identical. WHSV$^{-1}$: 15-40 (kg-cat s mol C$_3$H$_8$$^{-1}$) [h-BN]; 2-5 (kg-cat s mol C$_3$H$_8$$^{-1}$) [BNNT]; T=490° C., P$_{O2}$=0.15 atm, P$_{C3H8}$=0.3 atm (balance N$_2$).

Connell, *Nanoscale*, 4, 6908-6939 (2012); N. G. Chopra, R. J. Luyken, K. Cherrey, V. H. Crespi, M. L. Cohen, S. G. Louie, A. Zettl, *Science*, 269, 966-967 (1995); A. Pakdel, Y. Bando, D. Golberg, *Chem. Soc. Rev.*, 43, 934-959 (2014); A. L. Bezanilla, J. Huang, H. Terrones, B. G. Sumpter, *J. Phys. Chem. C*, 116, 15675-15681 (2012)). The combination of the interesting observations outlined in this example (i.e. improved selectivity to olefins and different reaction kinetics) points towards a novel, fundamentally different reaction mechanism compared to other, well-studied catalysts. Metal impurities in the material are unlikely to play a significant role. Indeed, various boron nitride samples from various suppliers, containing different impurities (FIG. 12) show almost identical catalytic performance (FIGS. 13-14).

Based on semiconductor literature focusing on oxygen-terminated armchair edges of BN (A. L. Bezanilla, J. Huang, H. Terrones, B. G. Sumpter, *J. Phys. Chem. C*, 116, 15675-15681 (2012)), as well as the proposed active sites of graphene and fullerene materials for other oxidations (J. Zhang, X. Liu, R. Blume, A. Zhang, R. Schlogl, D. S. Su, *Science*, 322, 73-77 (2008); B. Frank, J. Zhang, R. Blume, R. Schogl, D. S. Su, *Angew. Chem. Int. Ed.*, 48, 6913-6917 (2009)), we propose an oxygen-terminated armchair edge of BN (>B—O—O—N<) as the active site for the ODHP reaction. In line with the observed oxygen-dependence of the kinetics, we propose that an oxygen molecule bonded to one B and one N atom acts as the active site. These >B—O—O—N< sites can be viewed as inorganic peroxide species, able to perform oxidation reactions.

The second order rate dependence with respect to $P_{C3H8}$ suggests that two propane molecules are required to generate two molecules of water, in line with the overall stoichiometry of the reaction. The desorption of these water molecules forms BN edge vacancies allowing for unique $O_2$ activation, explaining the influence that the surface coverage of adsorbed oxygen has on the rate of propane consumption.

In summary, this example identifies boron nitride, typically assumed to be inert, as a hitherto unexplored oxidation catalyst. Exceptional selectivity towards propene was obtained during the oxidative dehydrogenation of propane.

Materials and Methods.

Hexagonal boron nitride (h-BN, Sigma-Aldrich & Alfa-Aesar) and boron nitride nanotubes (BNNT, BNNT, LLC) were used as provided without further chemical or thermal treatment. Multiple h-BN batches and suppliers were used to ensure reproducibility, and to confirm that it is truly the BN material responsible for catalysis, rather than a potential metal impurity. All suppliers guarantee >99% purity of h-BN and BNNT, which is confirmed with our own metal impurity analysis using induced coupled plasma optical emission spectroscopy (ICP-OES) (FIG. 12).

Acid digestion of BN materials was completed by refluxing ~10 mg BN in 6 mL aqua regia solution (3:1 HCl:HNO3) overnight, followed by gravity filtration and dilution of collected acid with 34 mL $H_2O$ (18 MΩ). The collected solution was then analyzed using an Optima 2000 DV optical emission spectrometer (Perkin Elmer Instruments), screening for metals including Fe, Ca, Al, Ti, Ni, Pt, V, Cu, Zr, Ga, Mo, Ag, and Na. While the quantity of metal impurities in h-BN samples vary among batches and suppliers, the catalytic response between them does not (FIGS. 13-14), ensuring the trace metal impurities do not influence the catalysis significantly.

The supported vanadia on silica catalyst (V/$SiO_2$, 4.5 wt % vanadium) was prepared using well described incipient wetness impregnation procedures, involving the introduction of vanadium oxytriisopropoxide (Sigma-Aldrich) diluted in isopropanol (Sigma-Aldrich) to the $SiO_2$ (Aerosil200, Evonik) surface with subsequent calcination at 550° C. The volume of the vanadium oxytriisopropoxide/isopropanol solution was equivalent to the pore volume of the $SiO_2$. Raman spectroscopy was used to ensure two-dimensional dispersion of surface vanadia species, which allows considerably higher selectivity to propene than material containing three-dimensional $V_2O_5$ nanoparticles.

Powder h-BN and V/$SiO_2$ catalysts were compressed using a pellet press (Pike Technologies) and sieved to collect particles of 600-710 μm diameter in order to limit any potential mass transfer effects. About 150 mg V/$SiO_2$ and 300 mg inert SiC particles (thermal conductor) were loaded into a quartz reactor tube (9 mm diameter), while about 300 mg h-BN was loaded into the reactor tube without SiC. About 40 mg BNNT (un-pressed) was diluted with about 100 mg inert $SiO_2$ particles to ensure a uniform bed. Flowrates of propane (industrial grade, Airgas), oxygen (UHP, Airgas) and nitrogen (UHP, Airgas) were controlled using three mass flow controllers (Bronkhorst) and calibrated to each individual gas to allow total flowrates of 40-160 mL min-1. The reactor tube was loaded into a Microactivity-Effi reactor setup, which included a tube furnace capable of maintaining temperatures up to 1100° C. and a liquid-gas separator to condense formed water. The reactor effluent was analyzed using a Shimadzu 2010 GC equipped with three Restek columns (Rtx-1, RT-Msieve 5A, and Rt-Q-Bond) and a thermal conductivity detector (TCD) as well as a flame ionization detector (FID). The carbon balance of each data point closes within 2%.

Equations.

Propane conversion, X, is calculated as follows:

$$X = \frac{\sum F_{carbon, prod}}{F_{C3H8,in}}$$

where $F_{carbon\ prod}$=flow of all carbon from products out of reactor (mol $s^{-1}$ g-cat$^{-1}$)

$F_{C3H8,in}$=flow of propane into the reactor (mol $s^{-1}$ g-cat$^{-1}$)

Product selectivity, S, is calculated as follows:

$$S = \frac{F_{A,out}}{\sum F_{carbon\ prod}}$$

where $F_{A,out}$=flow of carbon in product A out of reactor (mol $s^{-1}$ g-cat$^{-1}$)

$F_{carbon\ prod}$=flow of all carbon from products out of reactor (mol $s^{-1}$ g-cat$^{-1}$)

Inverse weight-hour-space-velocity, WHSV$^{-1}$ (kg-cat s mol $C_3H_8^{-1}$), is calculated as follows:

$$WHSV^{-1} = \frac{M_{cat} * (V/n)_{STP}}{F_{total} * N_{C3H8}}$$

where $M_{cat}$=mass of catalyst loaded in reactor (kg)

$(V/n)_{STP}$=24.5 (L/mol) at 298.15 K (1 atm, R=8.206*$10^{-2}$ L atm K$^{-1}$ mol$^{-1}$)

$F_{tot}$=total flow of all inlet gasses (L s$^{-1}$)

$N_{C3H8}$=mol percent propane in gas feed (mol %)

Example 6: Nickel Boride as an Additional Active Catalysts for ODHP

In this example, we extend the ODHP catalyst assays disclosed in Example 4 to further include Ni-boride. As outlined in Example 4, various boron- or nitride-containing catalysts were screened for oxidative propane dehydrogenation (ODHP) activity, including B-nitride, Ti-nitride, Al-nitride, B-carbide, Ti-boride, and Nb-boride. In this example, we also demonstrate the catalytic activity of Ni-boride activity.

Operating conditions were as follows: $P_{O2}$=0.15 atm, $P_{C3H8}$=0.3 atm, $P_{N2}$=0.55 atm, T=490° C. Due to differences in the reactivity between catalysts, total inlet flow rates between catalysts fluctuated between 40 and 140 mL min$^{-1}$, in order to achieve ~5% propane conversion. About 200 mg of boron- or nitride-containing catalysts 600-710 μm in size were loaded in a 9 mm inner diameter quartz reactor. All carbon balances close to within ±5%.

All the tested boron- or nitride-containing catalysts, including Ni-boride, showed activity for ODHP. Furthermore, all the tested boron-containing catalysts, including Ni-boride, display high selectivity to propene, with the primary byproduct being ethylene.

Inlet flowrates of the $C_3H_8/O_2/N_2$ gas mixture past the screened boron-containing, nitride-containing and V/SiO$_2$ catalysts were varied to achieve a range of propane conversions. Operating conditions were as follows: $P_{O2}$=0.15 atm, $P_{C3H8}$=0.3 atm, $P_{N2}$=0.55 atm, T=490° C. About 200 mg of boron- or nitride-containing catalysts 600-710 μm in size were loaded in a 9 mm inner diameter quartz reactor with total inlet flowrates of 40-140 mL min$^{-1}$, equivalent to WHSV$^{-1}$ of 100-300 kg-cat s m$^{-3}$. All carbon balances close to within ±5%.

Figure 15:
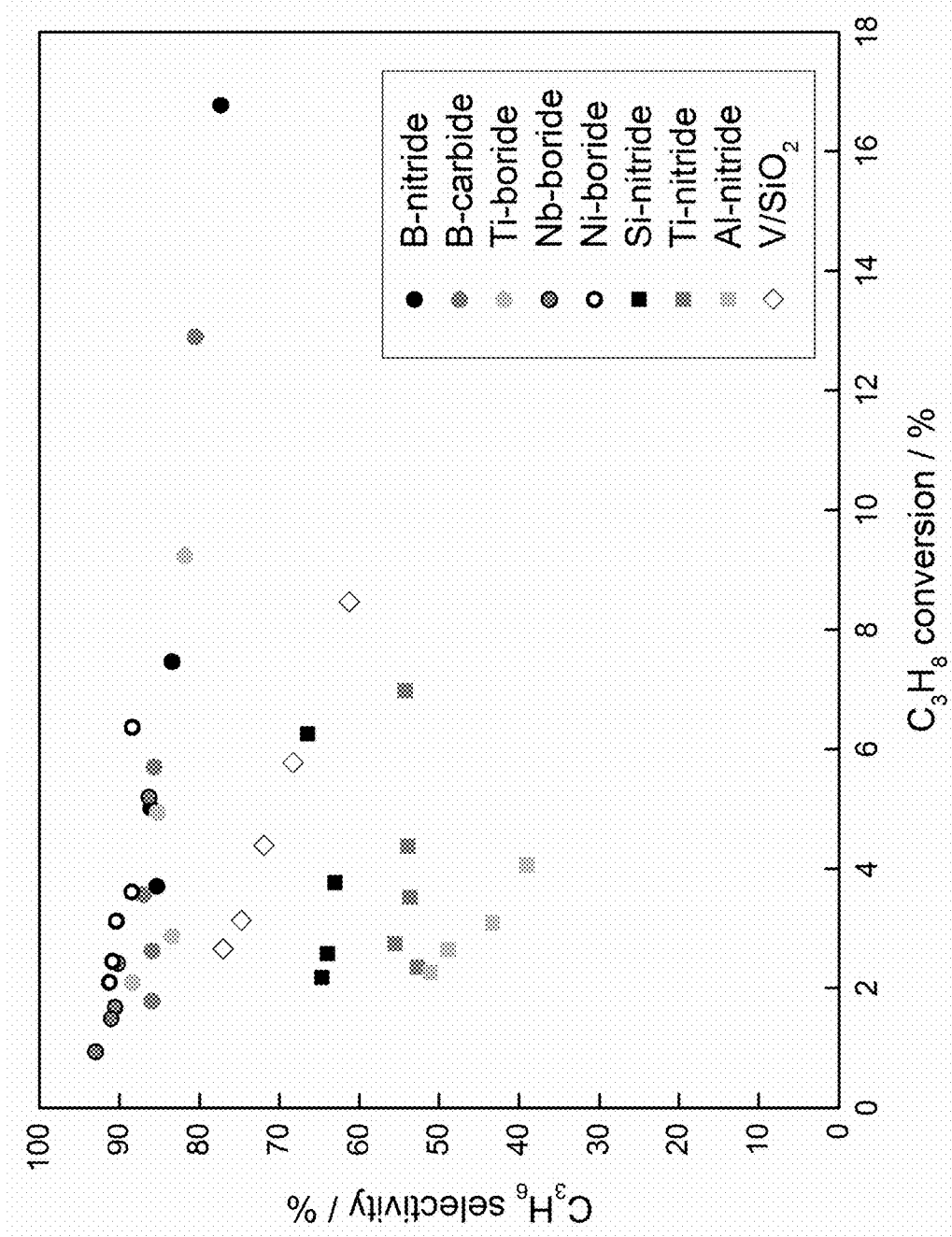
FIG. 15 is a graph showing that both boron- and nitride-containing catalysts, including nickel boride (Ni-boride) show activity for oxidative dehydrogenation of propane (ODHP); T=490° C., P$_{O2}$=0.15 atm, P$_{C3H8}$=0.3 atm.

As shown in FIG. 15, the boron-containing catalysts, including Ni-boride, maintained high propene selectivity even at high propane conversions. In sum, this example provides additional data supporting the Example 4 conclusion that a variety of boron- and nitride-containing catalyst can be used to catalyze the oxidative dehydrogenation of short chain alkanes to corresponding olefins.

Example 7: Selective Oxidative Dehydrogenation of n-Butane to 1-Butene and 2-Butene Using BNNTs In this example, we demonstrate BNNT-catalyzed ODH using n-butane as the alkane reactant, resulting in a mixture of alkene products, 1-butene and 2-butene. The results demonstrate that the disclosed methods are not limited to ODH of propane (ODHP), but can instead be generalized to ODH of other alkanes to yield the corresponding alkenes.

In the ODH of n-butane, n-butane is dehydrogenated in the presence of oxygen to yield a mixture of 1-butene and 2-butene. Water is also produced. As noted previously, ODH produces undesirable byproducts, such as CO; thus, ODH catalysts demonstrating increased selectivity towards the desired alkene products (in this case, the C4 butenes, 1-butene and 2-butene) are preferred.

Figure 16:
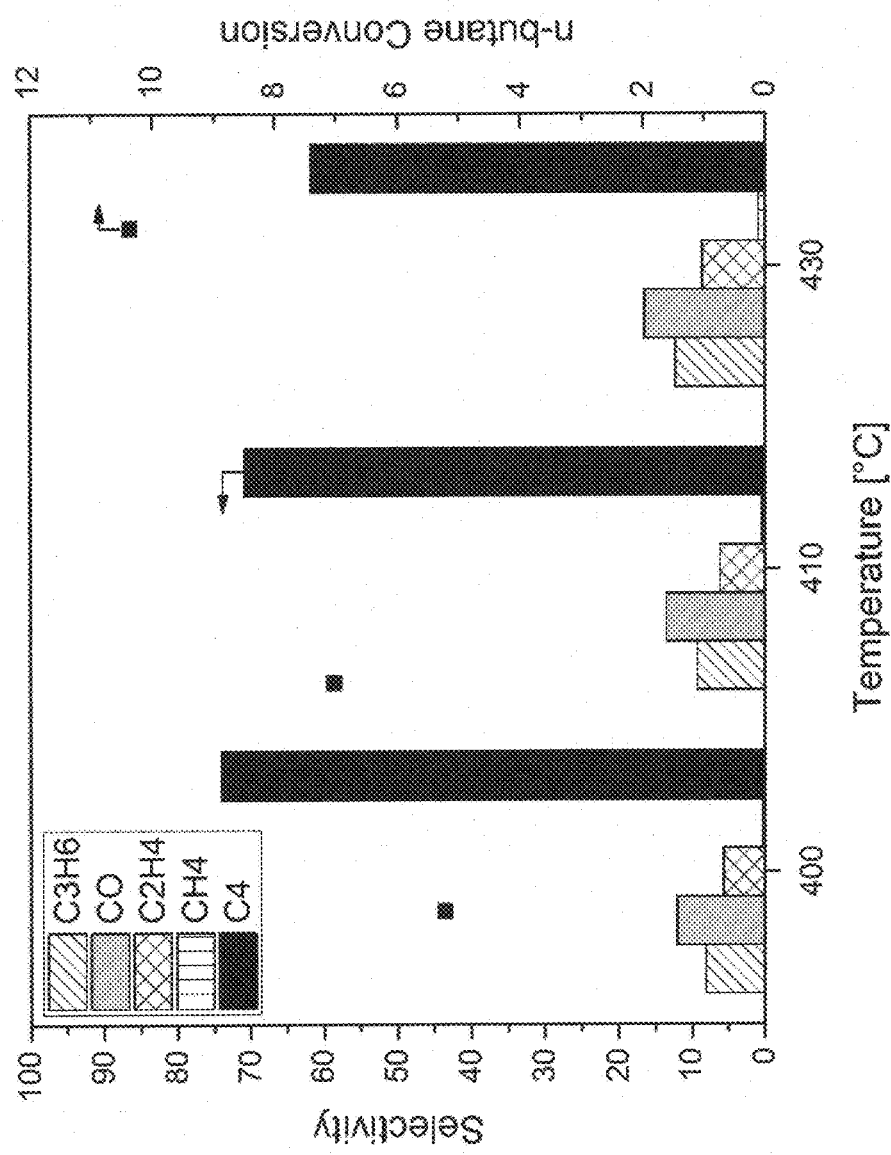
FIG. 16 is a graph showing BN nanotube n-butane ODH conversion (black squares, right axis) and product selectivity (bars, left axis) as a function of reaction temperature. C4 selectivity combines selectivity to 1-butene and 2-butenes.
Figure 17:
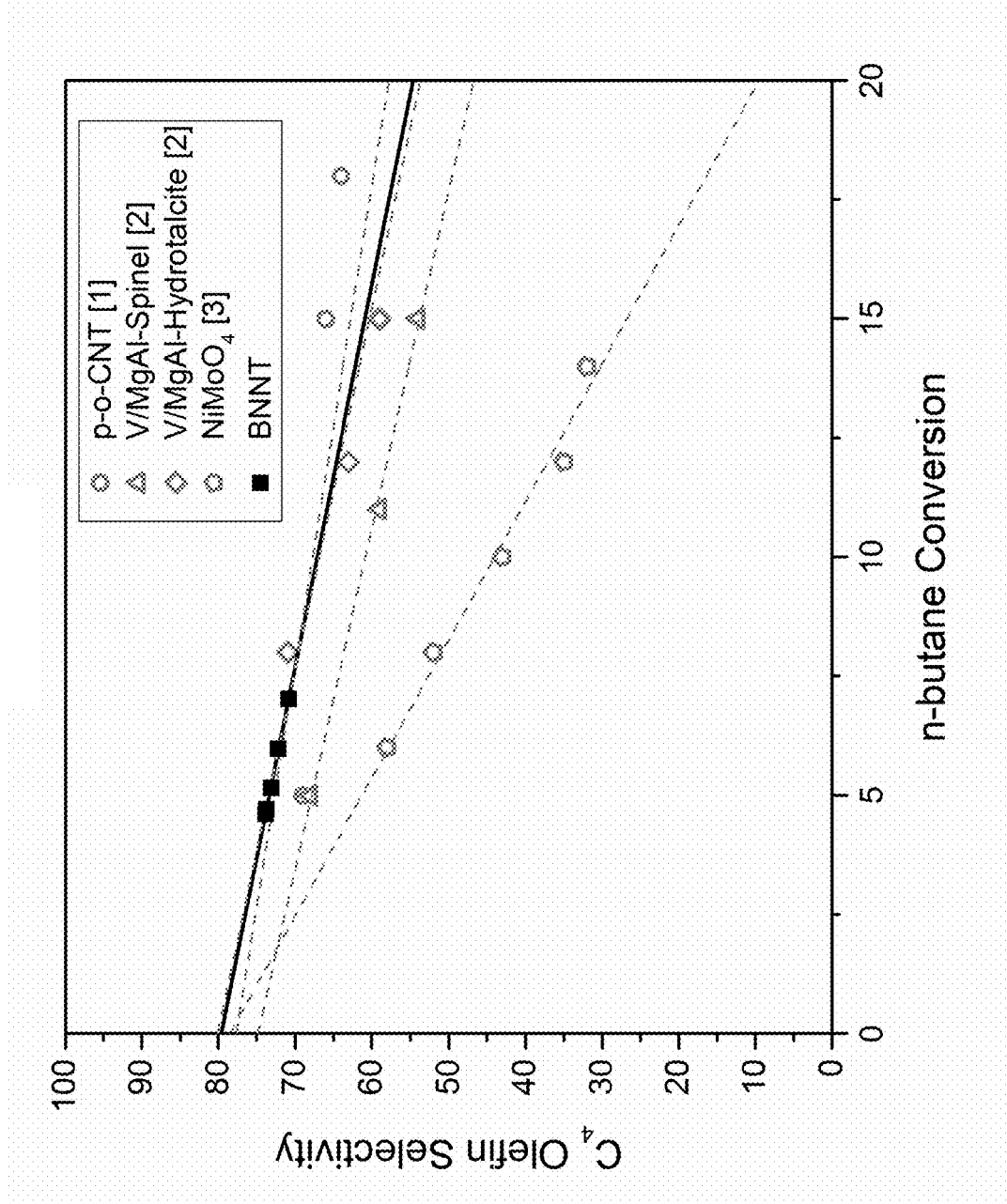
FIG. 17 is a graph comparing BN nanotube n-butane ODH conversion (x-axis) and C4 selectivity (y-axis) with reported state of the art catalysts. p-o-CNT denotes functionalized carbon nanotubes. BNNTs show comparable selectivity to the most selective catalysts reported. Open symbols indicate reactivity data from other works, cited within the FIG. 1-3; 1: Zhang, J.; Liu, X.; Blume, R.; Zhang, A.; Schlogl, R.; Su, D. S. *Science.* 2008, 322 (5898), 73-77; 2: Nieto, J. M. L.; Concepcion, P.; Dejoz, a; Knozinger, H.; Melo, F.; Vazquez, M. I. *J. Catal.* 2000, 189 (1), 147-157; 3: Madeira, L. M.; Portela, M. F. *Catal. Rev.* 2002, 44 (2), 247-286.).

Using the general methods outlined in the previous examples (see, e.g., Example 1 and Example 5), we assayed the ODH catalytic activity of BNNTs, using n-butane as the alkane reactant. We determined the resulting ODH % conversion of n-butane and the product selectivities as a function of reaction temperature (FIG. 16, temperatures on x-axis; n-butane conversion shown as black squares with values shown on the right side; selectivities shown as bars with values on the left side; C4 is 1-butene plus 2-butene). As seen in FIG. 17, BNNTs show favorable selectivity towards the desired C4 products.

We compared the BNNT n-butane ODH conversion and C4 selectivity data with the values reported for previously disclosed n-butane ODH catalysts (functionalized carbon nanotubes (p-o-CNT), V/MgAl-Spinel, V/MgAl-Hydrotalcite, and NiMoO$_4$). As seen in FIG. 17, BNNT shows comparable selectivity (see solid line) to the most selective previously reported n-butane catalysts.

Example 8: Selective Oxidative Dehydrogenation of Isobutane to Isobutene Using h-BN and BNNTs This example illustrates BN- and BNNT-catalyzed ODH using isobutane as the alkane reactant, resulting in isobutene as the alkene product. The results provide additional data demonstrating that the disclosed methods can be generalized to ODH of a variety of alkanes to yield the corresponding alkenes.

In the ODH of isobutane, isobutane is dehydrogenated in the presence of oxygen to yield isobutene. Water is also produced. As noted previously, ODH produces undesirable byproducts, such as CO and $CO_2$; thus, ODH catalysts demonstrating increased selectivity towards the desired alkene product (in this case, isobutene) are preferred.

Using the general methods outlined in the previous examples (see, e.g., Example 1 and Example 5), we assayed the ODH catalytic activity of both h-BN and BNNTs, along with V/SiO$_2$, a known isobutene ODH catalyst, using isobutane as the alkane reactant. Reaction conditions were: WHSV$^{-1}$: 16-48 (kg-cat s mol $C_4H_{10}^{-1}$) [V/SiO$_2$]; 44-111 (kg-cat s mol $C_4H_{10}^{-1}$) [h-BN]; 4-12 (kg-cat s mol $C_4H_{10}^{-1}$) [BNNT]; T=440° C., $P_{O2}$=0.1 atm, $P_{C4H10}$=0.1 atm (balance $N_2$).

Figure 18:
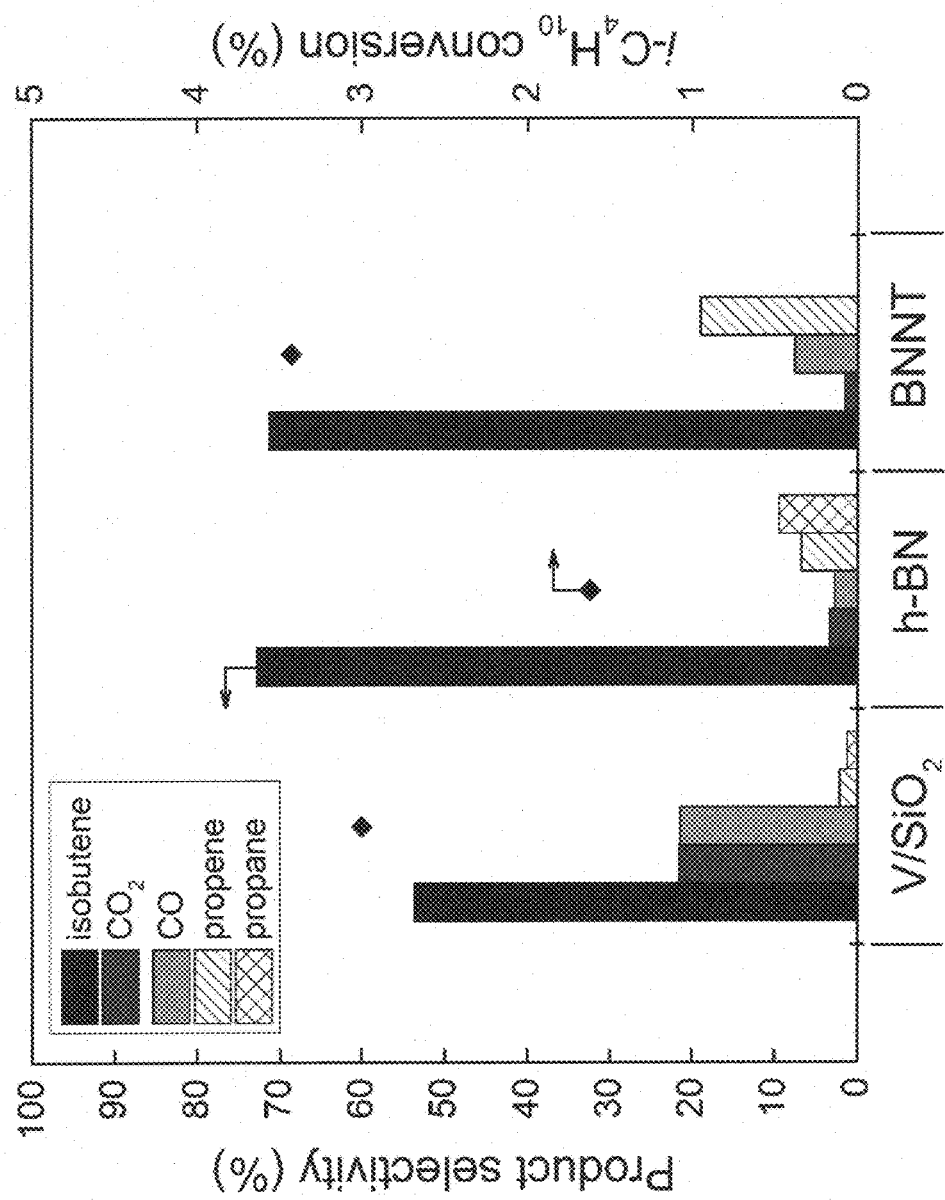
FIG. 18 is a graph showing comparisons of isobutane conversion (diamonds, right-axis) and product selectivity (bars, left-axis) when using vanadium oxide supported on silica ($V/SiO_2$), hexagonal BN (h-BN), and BN nanotubes (BNNT) as catalysts for ODH of isobutane. BN materials show much higher selectivity to olefins than the traditional $V/SiO_2$ catalyst, which shows high selectivity to $CO_x$ (~40%). $WHSV^{-1}$: 16-48 (kg-cat s mol $C_4H_{10}^{-1}$) [$V/SiO_2$]; 44-111 (kg-cat s mol $C_4H_{10}^{-1}$) [h-BN]; 4-12 (kg-cat s mol $C_4H_{10}^{-1}$) [BNNT]; T=440° C., $P_{O2}$=0.1 atm, $P_{C4H10}$=0.1 atm (balance $N_2$).

The resulting ODH % conversion of isobutane and the product selectivities for each catalyst are shown in FIG. 18 (catalyst used on x-axis; isobutane conversion shown as black squares with values shown on the right side; selectivities shown as bars with values on the left side). As seen in FIG. 18, both BN materials (h-BN and BNNTs) show much higher selectivity to olefins than the traditional V/SiO$_2$ catalyst, which shows an undesirable high selectivity towards $CO_x$ (~40%).

Figure 19:
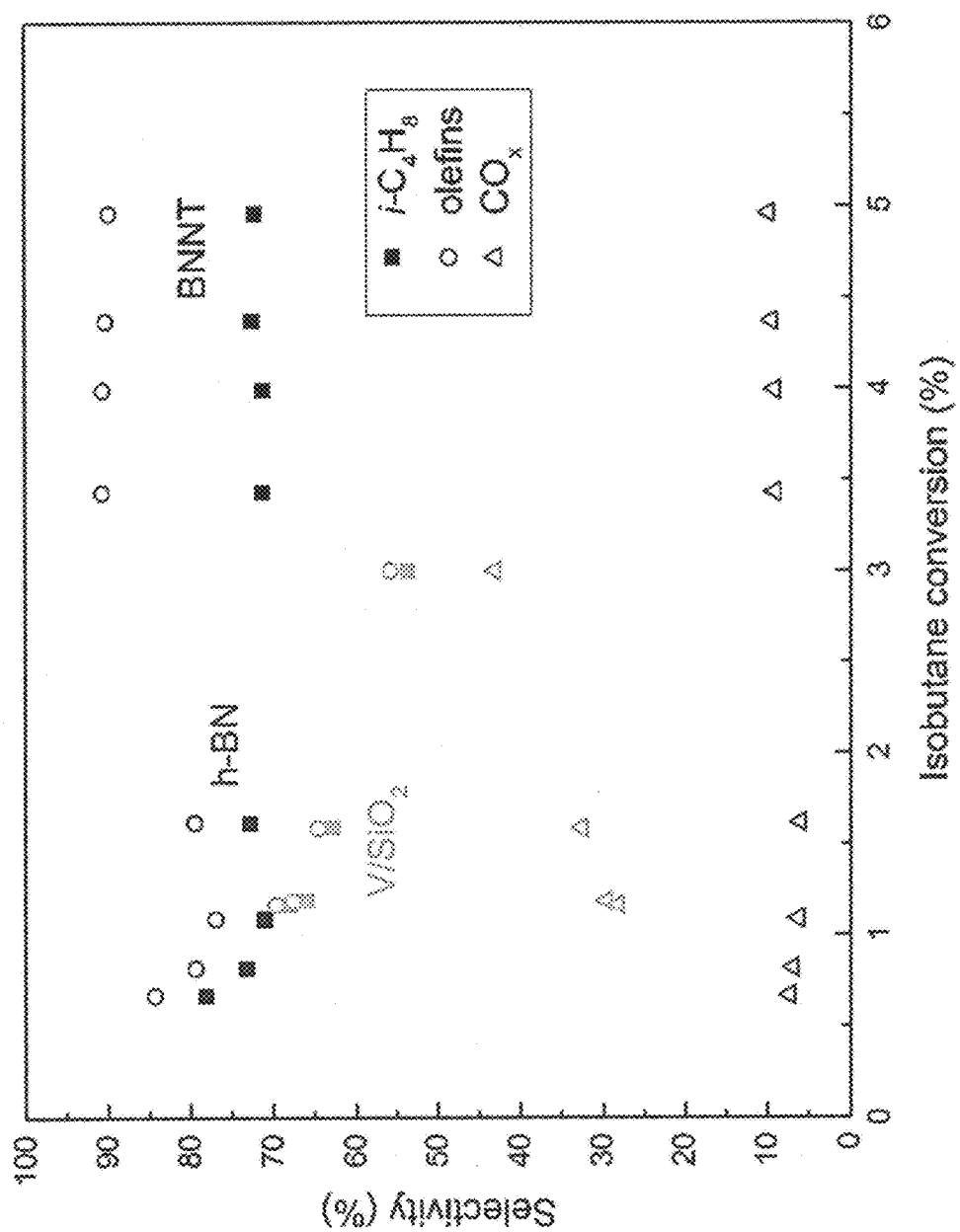
FIG. 19 is a graph showing product selectivity (y-axis) plotted against isobutane conversion (x-axis) when using vanadium oxide supported on silica ($V/SiO_2$), hexagonal BN (h-BN), and BN nanotubes (BNNT) as catalysts for ODH of isobutane. WHSV-1: 16-48 (kg-cat s mol $C_4H_{10}^{-1}$) [$V/SiO_2$]; 44-111 (kg-cat s mol $C_4H_{10}^{-1}$) [h-BN]; 4-12 (kg-cat s mol $C_4H_{10}^{-1}$) [BNNT]; T=440° C., $P_{O2}$=0.1 atm, $P_{C4H10}$=0.1 atm (balance $N_2$).

We plotted product selectivity as a function of isobutane conversion for the three ODH catalysts, and the results are shown in FIG. 19. Again, the results show that both h-BN and BNNT catalysts have higher selectivity for the favored olefin products (including, but not limited to, isobutene), and lower selectivity towards the undesired $CO_x$ products than the conventional catalyst.

Example 9: Oxygen Functionalization of the BN Surface Increases Catalyst Activity In this example, we demonstrate that the ODH-promoting activity of BN catalysts can be improved by bonding (i.e., functionalizing) oxygen to the BN surface. The BN surface can be functionalized with oxygen using one or more of a number of methods known in the art.

One such method is to contact the BN with nitric acid. We refluxed h-BN in concentrated $HNO_3$ for 2 hours. The resulting oxidized BN material was recovered by vacuum filtration and dried in an oven overnight. We then investigated the catalytic activity of the resulting oxygen functionalized material using the oxidative dehydrogenation of propane (ODHP) reaction, as described generally in the previous examples (see, e.g., Example 5).

Figure 20:
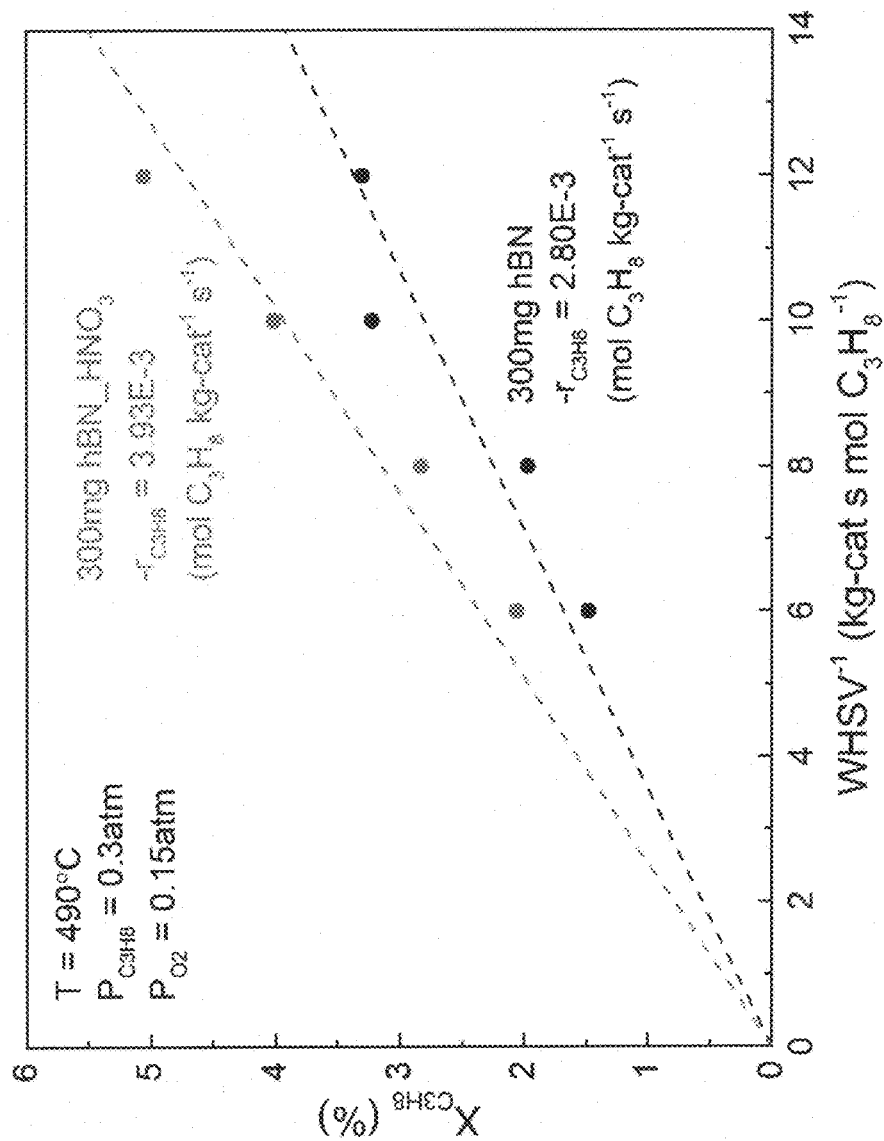
FIG. 20 is a graph showing propane consumption when using untreated h-BN (hBN) and oxygen functionalized h-BN (hBN_$HNO_3$) as ODHP catalysts. Oxygen functionalized h-BN shows ~40% higher rate of propane consumption as compared to untreated h-BN.

As seen in FIG. 20, the oxygen functionalized ($HNO_3$-treated) h-BN shows ~40% increase in the rate of propane consumption over an untreated h-BN material. XPS data confirms that the treated surface was in fact functionalized with oxygen. Specifically, the $HNO_3$-treated h-BN contains 3.83% (atom %) surface oxygen, while the untreated h-BN only contains 2.51% (atom %) surface oxygen.

In sum, this example demonstrates that the ODH catalytic activity of boron- and nitride-containing catalyst can be further improved by bonding oxygen to (i.e., functionalizing with oxygen) the catalyst surface.

Example 10: BN Catalyzed Oxidative Dehydrogenation of Ethylbenze

This example illustrates BN-catalyzed ODH using ethylbenzene as the alkyl group-containing reactant, resulting in styrene as the corresponding alkenyl-group containing product. The results provide additional data demonstrating that the disclosed methods can be generalized to ODH of alkyl groups attached to an aromatic ring, to yield the corresponding alkenyl group.

We were able attain a saturated ethylbenzene feed into a quartz reactor by bubbling nitrogen through an ethylbenzene saturator kept heated at 50° C. The furnace of the quartz reactor tube could be varied to 250-500° C., while the surrounding atmosphere from the quartz reactor tube furnace was heated to 160° C. Stainless steel tubing from the liquid saturator to the reactor unit and the reactor unit to the gas chromatograph (GC) was kept heated at 220° C. Nitrogen flow through the saturator was kept constant at 50 mL min$^{-1}$, while $O_2$ flow was kept constant at 5 mL min$^{-1}$, to give overall feed concentrations as 9% $O_2$, 2.7% ethylbenzene (balance $N_2$).

The ethylbenzene conversion and product selectivity are displayed in Table 1, comparing the gas-phase reactions of a blank quartz reactor tube (only quartz wool) and a quartz tube containing h-BN. Even at 500° C., ethylbenzene conversion is marginal without h-BN present and increases to 27% conversion in the presence of h-BN, showing low selectivity to $CO_x$ and high selectivity to all other important products (mostly styrene, benzene, toluene).

TABLE 1

ODH of ethylbenzene activity of a quartz reactor tube with and without h-BN

| Material | Temperature [° C.] | Ethylbenzene Conversion [%] | Product Selectivity [%] | | |
|---|---|---|---|---|---|
| | | | Styrene + Benzene + Toluene + others | $CO_2$ | CO |
| Blank Tube | 480 | 3.8 | 98.1 | 0.8 | 1.1 |
| | 500 | 6.0 | 97.2 | 0.5 | 2.3 |
| h-BN | 480 | 21.0 | 99.4 | 0.2 | 0.4 |
| | 500 | 27.4 | 97.9 | 0.4 | 1.7 |

Example 11: Oxidative Coupling of Methane Using h-BN

This example illustrates the use of h-BN as catalyst for the oxidative coupling of methane (OCM) into ethane and ethylene products. The results show that the disclosed methods can be used for other types of oxidations beyond ODH.

In OCM, two methane molecules are coupled to form ethane and ethylene. During this process, water is also produced. The activation of methane requires significantly higher temperatures than ODH, typically above 700° C. These high temperatures lead to the over oxidation of reaction products into CO and $CO_2$. Thus, catalysts that can show activity (i.e. activating methane) while minimizing over oxidation products are desirable.

Using similar analytical methods as in the previous examples, we assayed the catalytic activity of h-BN and compared it with that of catalytically inert quartz chips. Any activity observed during the quartz chip experiment was deemed to originate from gas phase methane activation. To minimize gas phase reactions, quartz wool was used to fill the void space past the catalyst bed. The reaction conditions were: WHSV-1=9-14 (kg-cat s mol $CH_4^{-1}$); T=750° C., 770° C.; $PO_2$=0.20 atm, $P_{CH4}$=0.4 atm (balance $N_2$).

The resulting OCM % conversion and selectivity towards coupling products (i.e. ethane and ethene) and COx products are shown in Table 2. At same flow rates and temperatures, the h-BN catalyst shows an increase in methane conversion of up to 55% when compared to the activity observed with the quartz chips. The h-BN catalyst's higher methane activation ability leads to a slightly lower C2 selectivity due to the over oxidation of the ethane and ethylene products. Despite this loss of selectivity, the overall C2 yields are higher than with the quartz chips.

TABLE 2

OCM activity of h-BN and inert quartz chips

| Material | Temperature [° C.] | Total Flow [mL/min] | Conversion [%] | Product Selectivity [%] | | | $C_2H_4/C_2H_6$ Ratio |
|---|---|---|---|---|---|---|---|
| | | | | $C_2$ | CO | $CO_2$ | |
| Quartz Chips | 750 | 80 | 5.5 | 49.0 | 48.9 | 1.1 | 0.7 |
| | | 100 | 3.7 | 50.3 | 48.4 | 0.8 | 0.5 |
| | | 120 | 2.2 | 52.9 | 46.1 | 0.6 | 0.3 |
| | 770 | 80 | 9.0 | 47.7 | 49.5 | 1.4 | 1.1 |
| | | 100 | 5.8 | 50.8 | 47.0 | 1.1 | 0.8 |
| | | 120 | 4.1 | 52.9 | 45.4 | 0.9 | 0.6 |
| h-BN | 750 | 80 | 13.2 | 40.1 | 57.0 | 1.7 | 1.2 |
| | | 100 | 8.2 | 44.5 | 53.4 | 1.1 | 0.8 |
| | | 120 | 4.8 | 44.9 | 53.7 | 0.7 | 0.5 |
| | 770 | 80 | 20.1 | 37.9 | 58.7 | 2.3 | 1.6 |
| | | 100 | 12.6 | 43.3 | 54.2 | 1.3 | 1.2 |
| | | 120 | 8.5 | 46.6 | 51.4 | 0.9 | 0.9 |

The invention is not limited to the embodiments set forth in this disclosure for illustration, but includes everything that is within the scope of the claims. Furthermore, all documents cited in this disclosure are hereby incorporated by reference in their entirety and for all purposes as if fully set forth in this disclosure.

We claim:

1. A method of making one or more desired chemical products comprising contacting a solid heterogeneous oxidative dehydrogenation (ODH) catalyst selected from the group consisting of a B-nitride consisting of boron and nitride, a B-nitride that is functionalized with one or more oxygen atoms bound directly to the B-nitride surface, a B-carbide consisting of boron and carbide, a B-carbide that is functionalized with one or more oxygen atoms bound directly to the B-carbide surface, Ti-boride, Ni-boride, and Nb-boride with a composition comprising both (a) oxygen and (b) one or more liquid or gaseous reactants to catalyze the ODH of the one or more liquid or gaseous reactants to form the one or more desired chemical products.

2. The method of claim 1, wherein the one or more liquid or gaseous reactants include a $C_{3+}$ alkane or ethylbenzene.

3. The method of claim 2, wherein the $C_{3+}$ alkane is a $C_3$-$C_5$ n-alkane or a $C_3$-$C_5$ iso-alkane.

4. The method of claim 1, wherein the one or more liquid or gaseous reactants include an alkane or a hydrocarbon comprising an alkyl group, and wherein the one or more desired chemical products include one or more olefins or one or more hydrocarbons comprising an alkenyl group.

5. The method of claim 4, wherein the alkane is a $C_3$-$C_5$ n-alkane or a $C_3$-$C_5$ iso-alkane.

6. The method of claim 5, wherein the $C_3$-$C_5$ n-alkane or $C_3$-$C_5$ iso-alkane is selected from the group consisting of propane, n-butane, and isobutane, and wherein the one or more desired chemical products are selected from the group consisting of propene, isobutene, 1-butene, 2-butene and butadiene.

7. The method of claim 4, wherein the method maintains a greater than 70% selectivity for the desired chemical products at 10% to 20% conversion of the alkane.

8. The method of claim 7, wherein the method maintains a greater than 77% selectivity for the desired chemical products at 10% to 20% conversion of the alkane.

9. The method claim 4, wherein the alkane is propane and the desired chemical product is propene.

10. The method of claim 4, wherein the one or more desired chemical products further include ethylene.

11. The method of claim 10, wherein the method exhibits a higher selectivity towards ethylene than it does towards undesired CO or $CO_2$ byproducts.

12. The method of claim 11, wherein the method exhibits a 90% or greater selectivity for the ethylene and other desired products together.

13. The method of claim 4, wherein the one or more liquid or gaseous reactants include a hydrocarbon comprising an alkyl group.

14. The method of claim 13, wherein the hydrocarbon comprising an alkyl group is ethylbenzene, and wherein the one or more desired chemical products include styrene.

15. The method of claim 1, wherein the ODH catalyst is functionalized with one or more oxygen atoms bound directly to the compound surface.

16. The method of claim 1, wherein the ODH catalyst is a boron nitride consisting of boron and nitride or a boron nitride that is functionalized with one or more oxygen atoms bound directly to the boron nitride surface.

17. The method of claim 16, wherein the boron nitride has a surface area range of about 5 $m^2 g^{-1}$ to 550 $m^2 g^{-1}$, about 9 $m^2 g^{-1}$ to 550 $m^2 g^{-1}$, about 50 $m^2 g^{-1}$ to 550 $m^2 g^{-1}$, about 100 $m^2 g^{-1}$ to 500 $m^2 g^{-1}$, or about 100 $m^2 g^{-1}$ to 200 $m^2 g^{-1}$.

18. The method of claim 16, wherein the boron nitride is in the form of hexagonal boron nitride (h-BN), boron nitride nanomeshes (h-BN nanomeshes), boron nitride nanosheets (BNNSs), boron nitride nanoribbons (BNNRs) or boron nitride nanotubes (BNNTs).

19. The method of claim 1, wherein the solid heterogenous catalyst is not simultaneously contacted with nitrogen.

20. The method of claim 1, wherein the composition comprising both (a) oxygen and (b) one or more liquid or gaseous reactants is a reactant stream that is contacted with the solid heterogeneous catalyst, and wherein the reactant stream includes from 0% to 70% nitrogen by volume.

* * * * *